US009066965B1

(12) United States Patent
Kelley

(10) Patent No.: US 9,066,965 B1
(45) Date of Patent: Jun. 30, 2015

(54) PURIFIED LIMONIN GLUCOSIDE FOR PREVENTION AND TREATMENT OF CHRONIC DISEASES

(71) Applicant: The United States of America, as represented by the Secretary of Agriculture, Washington, DC (US)

(72) Inventor: Darshan Singh Kelley, Davis, CA (US)

(73) Assignee: The United States of Americas, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/037,216

(22) Filed: Sep. 25, 2013

Related U.S. Application Data

(60) Provisional application No. 61/707,801, filed on Sep. 28, 2012.

(51) Int. Cl.
*A61K 31/7028* (2006.01)
*A61K 31/7032* (2006.01)
*C07H 15/26* (2006.01)
*C07H 15/18* (2006.01)
*A61K 31/7048* (2006.01)

(52) U.S. Cl.
CPC ............ *A61K 31/7048* (2013.01); *C07H 15/18* (2013.01); *A61K 31/7032* (2013.01); *A61K 31/7028* (2013.01); *C07H 15/26* (2013.01)

(58) Field of Classification Search
None
See application file for complete search history.

(56) References Cited

U.S. PATENT DOCUMENTS

| 6,251,400 B1 * | 6/2001 | Guthrie et al. ................ 424/736 |
| 2006/0116509 A1 | 6/2006 | Manners et al. |
| 2007/0117763 A1 * | 5/2007 | Guthrie ........................... 514/27 |

OTHER PUBLICATIONS

Bo, S, et al., "Associations between gamma-glutamyl transferase, metabolic abnormalities and inflammation in healthy subjects from a population-based cohort: a possible implication for oxidative stress" World Journal of Gastroenterology (2005)11:7109-17.
Corti, A, et al., "Gamma-glutamyltransferase of cancer cells at the crossroads of tumor progression, drug resistance and drug targeting" Anticancer research (2010) 30:1169-81.
Dutta, A, et al., "Variability in the Upper Limit of Normal for Serum Alanine Aminotransferase Levels: A Statewide Study" Hepatology (2009) 50:1957-62.
Fentiman, I.S, "Gamma-glutamyl transferase: risk and prognosis of cancer" British Journal of Cancer (2012) 106:1467-8.
Ghouri, N., D. Preiss, and N. Sattar, "Liver enzymes, nonalcoholic fatty liver disease, and incident cardiovascular disease: a narrative review and clinical perspective of prospective data" Hepatology (2010) 52:1156-61.
Kazemi-Shirazi, L. et al., "Gamma glutamyltransferase and long-term survival: is it just the liver?" Clinical Chemistry (2007) 53:940-6.
Kojima, C. et al., "Serum Complement C3 Predicts Renal Arteriolosclerosis in Non-Diabetic Chronic Kidney Disease" Journal of Atherosclerosis and Thrombosis (2012) 19:854-61.
Manners, G.D., "Citrus Limonoids: Analysis, Bioactivity, and Biomedical Prospects" Journal of Agricultural and Food Chemistry (2007) 55:8285-94.
Mistry, D. and R.A. Stockley, "Gamma-glutamyl transferase: the silent partner?" Journal of Chronic Obstructive Pulmonary Disease (2010) 7:285-90.
Neuschwander-Tetri, B.A. et al., "Influence of Local Reference Populations on Upper Limits of Normal for Serum Alanine Aminotransferase Levels" Archives of Internal Medicine (2008) 168:663-6.
Oh, R.C. and T.R. Hustead, "Causes and evaluation of mildly elevated liver transaminase levels" American Family Physician (2011) 84:1003-8.
Pompella, A. et al., "The significance of serum gamma-glutamyltransferase in cardiovascular diseases" Clinical Chemistry and Laboratory Medicine : CCLM / FESCC (2004) 42:1085-91.
Pompella, A. et al., "Gamma-glutamyltransferase, redox regulation and cancer drug resistance" Current Opinion in Pharmacology (2007) 7:360-6.
Ruhl, C.E. and J.E. Everhart, "Upper Limits of Normal for Alanine Aminotransferase Activity in the United States Population" Hepatology (2012) 55:447-54.
Ruhl, C.E. and J.E. Everhart, "Elevated serum alanine aminotransferase and gamma-glutamyltransferase and mortality in the United States population" Gastroenterology ( 2009) 136:477-85.
Seebacher, V. et al., "Prognostic signifigance of gamma-glutamyltransferase in patients with endometrial cancer: a multicentre trial" British Journal of Cancer (2012)106:1551-5.
Strasak, A.M. et al. "Association of gamma-glutamyltransferase and risk of cancer incidence in men: a prospective study" Cancer Research (2008) 68:3970-7.
Strasak, A.M. et al., "Prospective study of the association of gamma-glutamyltransferase with cancer incidence in women" International Journal of Cancer (2008) 123:1902-6.

(Continued)

*Primary Examiner* — Eric Olson
(74) *Attorney, Agent, or Firm* — Elizabeth R. Sampson; Lesley Shaw; John D. Fado

(57) ABSTRACT

One exemplary embodiment of the disclosure provides methods and compositions for treating a subject suffering from Alcoholic Liver Disease, Non-Alcoholic Fatty Liver Disease, type 2 diabetes, metabolic syndrome, cardiovascular disease, chronic kidney disease, and certain cancers, or a combination thereof, by administering a therapeutically effective amount of purified liminoid glucoside or a pharmaceutically acceptable salt thereof to the subject. In another exemplary embodiment, the disclosure provides methods and compositions for treating a subject suffering from elevated circulating concentrations of liver enzymes wherein the liver enzymes are selected from gamma glutamyl transferase, alanine amino transferase, alkaline phosphatase and complement fraction 3 or a combination thereof, the method comprising administering a therapeutically effective amount of purified liminoid glucoside or a pharmaceutically acceptable salt thereof to the subject wherein the treating results in a decreased circulating concentration of the liver enzymes.

10 Claims, 1 Drawing Sheet

(56) References Cited

OTHER PUBLICATIONS

Strasak A.M. et al., "Prospective study of the association of serum gamma-glutamyltransferase with cervical intraepithelial neoplasia III and invasive cervical cancer" Cancer Research (2010) 70:3586-93.

Targher, G., "Elevated serum gamma-glutamyltransferase activity is associated with increased risk of mortality, incident type 2 diabetes, cardiovascular events, chronic kidney disease and cancer—a narrative review" Clinical Chemistry and Laboratory Medicine (2010) 48:147-57.

Van Hemelrijck, M. et al., "Gamma-glutamyltransferase and risk of cancer in a cohort of 545,460 persons—the Swedish AMORIS study" European Journal of Cancer (2011) 47:2033-41.

Walport, M.J., "Complement Second of two parts" The New England Journal of Medicine (2001) 344:1140-4.

Wree, A. et al., "Elevated gamma-glutamyltransferase is associated with mortality in lung transplantation for cystic fibrosis" Transplant International : Official Journal of the European Society for Organ Transplantation (2012) 25:78-86.

Yamada, J. et al., "Elevated serum levels of alanine aminotransferase and gamma glutamyltransferase are markers of inflammation and oxidative stress independent of the metabolic syndrome" Atherosclerosis (2006) 189:198-205.

Zhang, J.B. et al., "Prognostic significance of serum gamma-glutamyl transferase in patients with intermediate hepatocellular carcinoma treated with transcatheter arterial chemoembolization" European Journal of Gastroenterology & Hepatology (2011) 23:787-93.

Polterauer, S. "Relevance of gamma-glutamyltransferase—a marker for apoptotic balance—in predicting tumor stage and prognosis in cervical cancer" Gynecologic oncology (2011) 122:590-594.

* cited by examiner

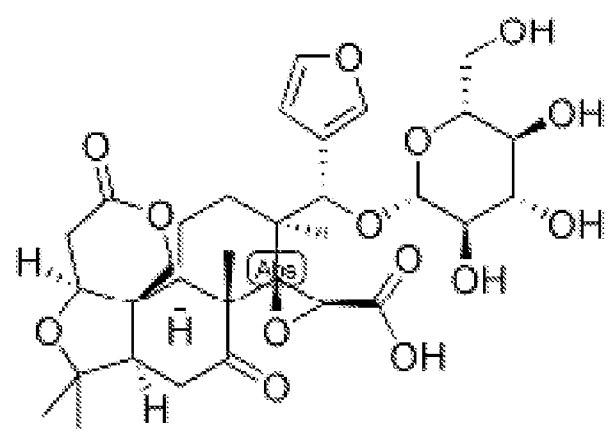

PURIFIED LIMONIN GLUCOSIDE FOR PREVENTION AND TREATMENT OF CHRONIC DISEASES

REFERENCE TO RELATED APPLICATIONS

This application claims priority to U.S. Provisional Patent Application U.S. Ser. No. 61/707,801, filed Sep. 28, 2012, which is incorporated herein by reference in its entirety.

FIELD OF THE INVENTION

The present invention relates to the use of purified limonoin glucoside for the treatment of chronic inflammatory diseases.

BACKGROUND OF THE INVENTION

Circulating concentrations of the hepatic enzymes gamma glutamyl transferase (GGT), alanine amino transferase (ALT), alkaline phosphatase (ALP) and complement fraction 3 (C3) are elevated in several human diseases including e.g., nonalcoholic fatty liver disease (NAFLD), alcoholic liver disease (ALD), metabolic syndrome (MS), type 2 diabetes (T2DM), cardiovascular disease (CVD), chronic kidney disease and cancer (see e.g., Ghouri N, et al. (2010) Hepatology, 52:1156-61; Oh R. C., Hustead T. R. (2011) American family physician 84:1003-8; Targher G. (2010) Clinical chemistry and laboratory medicine: CCLM/FESCC 48:147-57). Circulating concentrations of the hepatic enzymes are also increased in alpha antitrypsin deficiency, autoimmune hepatitis, Wilson's disease, thyroid disorders, celiac disease, hemolysis, and muscle disorders. These diseases are a major burden on the health systems worldwide and cost hundreds of billions of dollars yearly in management and loss of work.

Reference ranges for circulating hepatic enzymes vary with the gender, race, and the instrument used (see e.g., Dutta A., et al. (2009) Hepatology 50:1957-62; Neuschwander-Tetri B A, et al. (2008) Archives of internal medicine 168: 663-6). In fact, the upper limit of normal for ALT in USA varies two fold, possibly due to the use of markedly different or undefined reference population (see e.g., Ruhl C. E. and Everhart J. E. (2012) Hepatology 55:447-54). However, even within the so called normal ranges, elevations in liver GGT, ALT, and ALP are associated with chronic inflammatory diseases such as e.g., atherosclerosis, stroke, and CVD (see e.g., Mistry D., Stockley R. A. (2010) Journal of Chronic Obstructive Pulmonary Disease 7:285-90; Ghouri N. et al (2010) supra; Pompella A, et al. (2004) Clinical chemistry and laboratory medicine: CCLM/FESCC. 42:1085-91.) Indeed, mortality from T2DM, liver disease, CVD, cancer, and all causes increases 2-4 fold when individuals in the highest and lowest quartiles for GGT and ALT are compared (see e.g., Kazemi-Shirazi L., et al. (2007) Clinical chemistry 53:940-6; Targher G. (2010) supra; Ruhl C. E. and Everhart J. E. (2009) Gastroenterology. 136:477-85).

Furthermore, increased levels of GGT are associated with increased mortality in lung transplantation for cystic fibrosis (see e.g., Wree A., et al. (2012) Transplant international: official journal of the European Society for Organ Transplantation 25:78-86) and increased overall cancer risk (see e.g., Corti A., et al. (2010) Anticancer research. 30:1169-81; Pompella A. et al. (2007) Current opinion in pharmacology 7:360-6; Targher G. (2010) supra, Fentiman I. S. (2012) British journal of cancer 106:1467-8; Van Hemelrijck M., et al., (2011) Eur J Cancer 47:2033-41; Strasak A. M., et al. (2008) Cancer research 68:3970-7; Strasak A. M., et al. (2008) International journal of cancer Journal international du cancer 123:1902-6). Elevated levels of GGT are also associated with an increase the incidence of tissue specific types of cancers, including e.g., cervical (see e.g., Seebacher V., et al. (2012) British journal of cancer 106:1551-5; Polterauer S., et al., (2011) Gynecologic oncology 122:590-4; Strasak A. M., et al. (2010), Cancer research 70:3586-93), liver (see e.g., Zhang J. B., et al., (2011) European journal of gastroenterology & hepatology 23:787-93), prostate (see e.g., Van Hemelrijck M., et al., (2011) supra), Lungs (Wree A. et al. (2012) supra, Bechmann L. P., et al. (2012) Transplant international: official journal of the European Society for Organ Transplantation. 2012; 25:78-86.), digestive organs, lymphoid and hematopoietic cancers (see e.g., Targher G. (2010) supra; Corti A. et al. (2010) Anticancer research 30:1169-81).

Given the association of increased levels of liver enzyme with chronic disease, it is clear that a need exists for methods and compositions effective for reducing levels of liver enzymes. As will be clear from the following disclosure, the present invention provides for this and other needs.

SUMMARY OF THE INVENTION

In one aspect, the present disclosure provides a method of treating a subject suffering from elevated circulating concentrations of liver enzymes, wherein the liver enzymes are members selected from the group consisting of gamma glutamyl transferase (GGT), alanine amino transferase (ALT), alkaline phosphatase (ALP) and complement fraction 3 (C3) or a combination thereof, the method comprises administering to the subject a therapeutically effective amount of purified limonin glucoside (LG) or a pharmaceutically acceptable salt thereof, wherein the treating results in a decreased circulating concentration of at least one of the liver enzymes and with the proviso that the subject is not otherwise in need of treatment with limonin glucoside. In one exemplary embodiment, the treating results in a decreased circulating concentration of all four of the liver enzymes. In another exemplary embodiment, the treating results in a decreased circulating concentration of at least GGT and ALT. In another exemplary embodiment, the therapeutically effective dose of purified limonin glucoside is 0.5 grams per day and the dose results in a 33% decrease in the circulating concentration of GGT.

In another aspect, the present disclosure provides a method of treating a patient suffering from a chronic disease, wherein the chronic disease is a member selected from the group consisting of Alcoholic Liver Disease (ALD), Non-Alcoholic Fatty Liver Disease (NAFLD), type 2 diabetes, metabolic syndrome, cardiovascular disease (CVD), and chronic kidney disease (CKD), or a combination thereof, the method comprising administering a therapeutically effective amount of purified limonin glucoside (LG) or a pharmaceutically acceptable salt thereof. In one exemplary embodiment, the daily dose of (LG) or a pharmaceutically acceptable salt thereof for an adult is between about 0.05 g/day to about 5.0 g/day. In another exemplary embodiment, the dose is 0.5 gram per day. In another exemplary embodiment, the daily dose of (LG) or a pharmaceutically acceptable salt thereof for a child is between about 0.01 g/day to about 5.0 g/day. In still another exemplary embodiment, the purified limonin glucoside or a pharmaceutically acceptable salt thereof, is administered at a frequency of 4 or less times per day. In still another exemplary embodiment, the purified limonin glucoside or a pharmaceutically acceptable salt thereof, is administered two times per day. In one exemplary embodiment the purified limonin glucoside or a pharmaceutically acceptable salt thereof, is administered orally. In another exemplary embodiment, the chronic disease is NAFLD and wherein the purified limonin glucoside or a pharmaceutically acceptable salt thereof, is administered orally. In another exemplary embodiment, the administering results in a reduction in fat content of liver. In another exemplary embodiment, the administering results in a reduction in the incidence of or progression of cirrhosis. In another exemplary embodiment, the administering results in a reduction in the incidence of hepatocellular carcinoma.

In another aspect, the disclosure provides a pharmaceutical composition for treating a subject suffering from elevated circulating concentrations of liver enzymes, wherein the liver enzymes are members selected from the group consisting of gamma glutamyl transferase (GGT), alanine amino transferase (ALT), alkaline phosphatase (ALP) and complement fraction 3 (C3) or a combination thereof, wherein the treating results in a decreased circulating concentration of at least one of the liver enzymes and with the proviso that the subject is not otherwise in need of treatment with limonin glucoside, said composition comprising a pharmaceutically acceptable excipient and a therapeutically effective amount of purified limonin glucoside.

In another aspect, the disclosure provides a nutraceutical composition for treating a subject suffering from elevated circulating concentrations of liver enzymes, wherein the liver enzymes are members selected from the group consisting of gamma glutamyl transferase (GGT), alanine amino transferase (ALT), alkaline phosphatase (ALP) and complement fraction 3 (C3) or a combination thereof, wherein the treating results in a decreased circulating concentration of the liver enzymes and with the proviso that the subject is not otherwise in need of treatment with limonin glucoside, said composition comprising a pharmaceutically acceptable excipient and a therapeutically effective amount of purified limonin glucoside. In one exemplary embodiment, the composition is for prophylactic treatment.

Other features, objects and advantages of the invention will be apparent from the detailed description which follows.

BRIEF DESCRIPTION OF THE DRAWINGS

FIG. 1 shows a structural formula for limonin glucoside.

DETAILED DESCRIPTION OF THE INVENTION

Definitions

As used herein, the term "limonoid compound" refers to any limonoid based chemical compound. The term "limonoid compounds" refers inclusively to limonoid aglycones, limonoate A-ring lactones, limonoid glycosides including, but not limited to limonoid glucosides, limonoid carboxylic acids including, but not limited to limoinoid glycoside mono- and di-carboxylic acids.

The term "limonin glucoside" or "limonin-17-β-D-glucopyranoside" as used herein refers to, a liminoid glycoside having the chemical formula $C_{32}H_{42}O_{14}$. An exemplary structural formula depicting a limonin glucoside molecule is shown in FIG. 1.

The term "limonoid glycoside" refers to limonoid compounds that are carboxylic acid limonoids derived from hydrolyzed lactones, wherein the alcoholic oxygen of the hydrolyzed lactone ring is glycosolated. Thus, limonoid glycosides comprise derivatives of A-ring and D-ring δ-hydroxy carboxylic acid forms of *citrus* limonoids. In general, "limonoid glycosides" are limonoid A-ring lactones that contain one or more sugar moieties attached via a, β-glycosidic linkage at C-17. An exemplary limonoid glycoside is limonin glucoside which is shown in FIG. 1.

"Limonoid glycosides" typically occur as limonoid glycoside carboxylic acids. Typically, limonoid glycoside carboxylic acids occur in two carboxylic acid forms; mono-carboxylic acids or mono-acids, and di-carboxylic acids, or di-acids.

The term "isolated" refers to a material that is substantially or essentially free from components which are used to produce the material. For compositions disclosed herein, the term "isolated" refers to material that is substantially or essentially free from components which normally accompany the material in the mixture used to prepare the composition. "Isolated" and "pure" are used interchangeably. Typically, isolated limonin glucoside has a level of purity that, in exemplary embodiments, is expressed as a range. The lower end of the range of purity for the component is about 60%, about 70% or about 80% and the upper end of the range of purity is about 70%, about 80%, about 90% or more than about 90%. Thus, when limonin glucoside is more than about 90% pure, the purities are also preferably expressed as a range. The lower end of the range of purity is about 90%, about 92%, about 94%, about 96% or about 98%. The upper end of the range of purity is about 92%, about 94%, about 96%, about 98% or about 100% purity. Purity is determined by any art-recognized method of analysis (e.g., HPLC, or a similar means).

The term "liver enzymes" or "hepatic enzymes" as used herein refers to gamma glutamyl transferase (GGT, EC number 2.3.2.2), alanine amino transferase (ALT, EC number 2.6.1.2), alkaline phosphatase (ALP, EC number 3.1.3.1) and complement fraction 3 which is also known in the art as complement component 3 (C3, EC number 3.4.21.43) which are produced by the liver.

The expression "circulating concentrations of liver enzymes", "blood concentration of liver enzymes", "serum concentration of liver enzymes" or "plasma concentrations of liver enzymes" as used herein refers to the plasma or serum concentrations of liver enzymes. Methods for measuring circulating concentrations of liver enzymes are well known in the art, see e.g., Schiff s Diseases of the Liver, 11th Edition, Eugene R. Schiff, Willis C. Maddrey, Michael F. Sorrell eds. December 2011, Wiley-Blackwell.

The expression, "elevated circulating concentrations of liver enzymes" as used herein refer to circulating concentrations of liver enzymes that are above or within levels that are considered in the art to be high end of normal. Normal ranges for liver enzymes and thus, elevated circulating concentrations of liver enzymes are well known to persons skilled in the art (see e.g., Schiff's Diseases of the Liver, supra) and disclosed herein below.

The expression "decreased circulating concentration of liver enzymes" as used herein, refers to a reduction in the circulating concentration of liver enzymes by comparison to a baseline or initial level in a subject. A decrease in the circulating concentration of liver enzymes can be small or large. Thus, in exemplary embodiments, a decrease in the circulating concentration of liver enzymes is a decrease in the circulating concentration of one or more liver enzymes of about 1%, about 2%, about 3%, about 4%, about 5%, about 6%, about 7%, about 8%, about 9%, about 10%, about 15%, about 20%, about 25%, about 30%, about 35%, about 40%, about 50%, about 60%, about 70% or more. In some exemplary embodiments each of the one or more liver enzymes decrease by a different amount. Thus, in one exemplary embodiment, the circulating concentration of GGT is decreased by about 30%, the circulating concentration of ALP is decreased by about 10%, the circulating concentration of ALT is decreased by about 13%, and the circulating concentration of C3 is decreased by about 4.8%.

The term "ameliorate" refers to any indicia of success in the treatment of an injury, pathology or condition, including any objective or subjective parameter such as abatement; remission; diminishing of symptoms or making the injury, pathology or condition more tolerable or bearable to the patient or subject; slowing in the rate of degeneration or decline; making the final point of degeneration less debilitating; improving a patient's physical or mental well-being. The amelioration of symptoms can be based on objective or subjective parameters; including the results of a physical examination, and/or a psychiatric evaluation or any other appropriate means known in the art. For example, the methods disclosed herein successfully ameliorate a patient's NAFLD by decreasing the circulating blood concentrations of e.g., gamma glutamyl transferase (GGT). "Ameliorate" as used herein may also refer to the complete elimination of the symptoms of elevated liver enzymes e.g., reducing the circulating concentration of liver enzymes GGT, ALT, ALP, C3 from a concentration that is at or above high level normal to a concentration that is within low to mid-normal levels.

The term "to treat", "treating", "treatment" or "therapy" as used herein, refers to means for reducing/decreasing the circulating concentrations of at least one "liver enzyme" thereby eliminating disease and/or the accompanying symptoms in a subject. "Treating", "treatment" or "therapy" of a disease or condition includes preventing the disease or condition from occurring in a subject that may be predisposed to the disease, but does not yet experience or exhibit symptoms of the disease or condition (prophylactic treatment), inhibiting the disease (slowing or arresting its development), providing relief from the symptoms or side-effects of the disease or condition (including palliative treatment), and relieving the disease or condition (causing regression of the disease or condition).

The term "effective amount" or "an amount effective to" or a "therapeutically effective amount" or any grammatically equivalent term means the amount that, when administered to an animal or human for treating a disease or condition, is sufficient to effect treatment or therapy for that disease. Thus, a "therapeutically effective amount" or "effective amount" refers to that amount of the compound sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose or amount refers to combined amounts of the active ingredients that result in the therapeutic effect, whether administered in combination, including serially or simultaneously. In one embodiment, a therapeutically effective amount of purified limonin glucoside ameliorates symptoms, of e.g. NAFLD including symptoms such as e.g., increased fat content of liver, incidence of or progression of cirrhosis, incidence of hepatocellular carcinoma, increased hepatic aminotransferase levels, such as ALT and AST, and gamma-glutamyltransferase (gamma-GT), C3 etc.

The term "prophylactic" refers to an agent that acts to prevent disease, such as e.g., Non-Alcoholic Fatty Liver Disease (NAFLD). In one aspect, limonin glucoside is administered prophylactically to prevent the onset or recurrence of e.g, Alcoholic Liver Disease (ALD), non-alcoholic Fatty Liver disease (NAFLD), Cardiovascular disease (CVD), prostate cancer, metabolic syndrome, etc.

Prophylaxis is expected to be particularly relevant to the treatment of persons who have suffered a previous episode of, or are otherwise considered to be at increased risk of the disease or condition in question. Persons at risk of developing a particular disease or condition may include those having a family history of the disease or condition, or those who have been identified by genetic testing or screening to be particularly susceptible to developing the disease or condition.

In particular, the compounds disclosed herein (including pharmaceutically acceptable salts) may be used in the treatment of e.g., Alcoholic Liver disease (ALD), NAFLD, type 2 diabetes, CVD, chronic kidney disease, metabolic syndrome and certain cancers e.g., prostate cancer. The disclosure further provides methods of treating, or reducing the risk of, a disease or condition comprising or arising from elevated levels of gamma glutamyl transferase (GGT), alanine amino transferase (ALT), alkaline phosphatase (ALP) and complement fraction 3 (C3), which method comprises administering to a patient in need thereof a therapeutically effective amount of purified limonin glucoside or a pharmaceutically acceptable salt thereof.

A subject "not otherwise in need of treatment with limonin glucoside" is an individual subject or patient who is not being treated with purified limonin glucoside for any disorder accepted by the medical community to be effectively treatable with limonin glucoside. Conditions known in the art and accepted by the medical community to be effectively treatable with limonin glucoside include certain cancers e.g., colon cancer.

As used herein, the expression "pharmaceutically acceptable carrier" refers to any material, which when combined with the liminoid glucoside retains the liminoid glucoside' activity and is non-reactive with a subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions including such carriers are formulated by well known conventional methods.

As used herein, the term "administering," refers to suitable means of delivering limonin glucoside to a subject in need thereof. In an exemplary embodiment, "administering" a limonin glucoside to a subject in need thereof refers to oral administration. In another exemplary embodiment, "administering" a limonin glucoside to a subject in need thereof refers to administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, administration may be directly to the tumor and/or into tissues surrounding the tumor. Other modes of delivery include, but are not limited to, the use of liposomal formulations, intravenous infusion, transdermal patches, etc.

The term "enhanced" refers to any degree of betterment, augmentation embellishment, beautification, strengthening and/or improvement. For example the phrase "enhanced performance" indicates that performance is improved in one state, by comparison to another.

The term "improved" refers to a more desirable condition than previously existed, or alternatively, improved refers to state wherein a more desirable result is achieved under one set of conditions as compared with another. Improvement is demonstrated by any indicia of success, betterment, progression, or amelioration including any objective or subjective parameter such as abatement, remission, and/or diminishing of symptoms or an improvement in an individual's physical or mental well-being. Improvement can be based on objective or subjective parameters; including the results of a physical examination and/or a psychiatric evaluation.

I. Introduction

This disclosure pertains to the surprising discovery that purified limonin glucoside decreases levels of circulating concentrations of the liver enzymes gamma glutamyl transferase (GGT), alanine amino transferase (ALT), alkaline phosphatase (ALP) and complement fraction 3 (C3). Since elevations in these enzymes even within their normal ranges increase the incidences of Alcoholic Liver Disease (ALD), nonalcoholic fatty liver disease (NAFLD), metabolic syndrome (MS), type 2 diabetes, chronic kidney disease (CKD), cardiovascular disease (CVD), metabolic syndrome and certain cancers e.g., cervical, liver, prostate, lungs, digestive organs, lymphoid and hematopoietic cancers, administration of a therapeutically effective amount of limonin glucoside to a subject in need thereof is effective for treating ALD, NAFLD, metabolic syndrome, type 2 diabetes, CVD, chronic kidney disease, certain cancers and other conditions comprising or arising from or in association with increased circulating concentrations of the liver enzymes gamma glutamyl transferase (GGT), alanine amino transferase (ALT), alkaline phosphatase (ALP) and complement fraction 3 (C3).

In treating ALD, NAFLD, type 2 diabetes, CVD, chronic kidney disease, and other conditions, the methods disclosed herein can ameliorate, eliminate, reduce or prevent the symptoms of ALD, NAFLD, type 2 diabetes, CVD, chronic kidney disease, and other conditions comprising or arising from or in association with increased circulating concentrations of the liver enzymes gamma glutamyl transferase (GGT), alanine amino transferase (ALT), alkaline phosphatase (ALP) and complement fraction 3 (C3). In one embodiment, the methods disclosed herein comprise administering a therapeutically effective amount of limonin glucoside to a subject in need thereof to treat or prevent elevated levels of the liver enzymes GGT, ALT, ALP and/or C3 and thereby prevent and/or treat disorders and diseases associated with elevated levels of liver enzymes e.g., ALD, NAFLD, type 2 diabetes, CVD, chronic kidney disease, metabolic syndrome and etc. Thus, the methods disclosed herein are effective in treating any one or more of ALD, NAFLD, type 2 diabetes, CVD, chronic kidney disease, metabolic syndrome and certain cancers in an afflicted patient.

Although reference ranges for circulating hepatic enzymes may vary, typically circulating concentration above the Upper Limit of Normal (ULN) are suggestive of disease. Exemplary normal reference ranges are for GGT are 0-65 IU/L (adult males) and 0-45 IU/L (adult females), for ALT 6-63 IU/L (males) and 5-54 IU/L (females), for ALP 35-115 IU/L (both genders), for C3 0.92-2.10 mg/mL (both genders), wherein enzyme activity is expressed in international units (IU), the amount of enzyme that catalyzes the conversion of 1 µmole of substrate per minute and L is liters.

Chronic diseases such as Alcoholic Liver Disease (ALD), nonalcoholic fatty liver disease (NAFLD), type 2 diabetes, chronic kidney disease (CKD), cardiovascular disease (CVD) and certain cancers, cost the economy billions of dollars annually. These costs as well as the suffering of individuals with chronic illness could be avoided through more effective prevention and treatment.

Fortunately it has now been discovered that treating a subject in need thereof with a therapeutically effective amount of purified limonin glucoside (LG) significantly decreases circulating concentrations of liver enzymes (GGT, ALT, ALP, and C3). Thus, in one exemplary embodiment, supplementing the diets of overweight and obese human subjects, with purified limonin glucoside (LG) significantly decreases circulating concentrations of liver enzymes (GGT, ALT, ALP, and C3). As the methods disclosed herein provide for administering purified limonin glucoside and compositions comprising purified limonin glucoside as pharmaceuticals, routine means to determine limonin glucoside drug regimens and formulations to practice the methods disclosed herein are set forth below.

II. Diagnosis of Disorders and Diseases Associated with Increased Levels of Gamma Glutamyl Transferase (GGT), Alanine Amino Transferase (ALT), Alkaline Phosphatase (ALP) and Complement Fraction 3 (C3)

Alcoholic Liver Disease and Non-Alcoholic Fatty Liver Disease

Non-alcoholic fatty liver disease (NAFLD) is one cause of a fatty liver, occurring when fat is deposited (steatosis) in the liver not due to excessive alcohol use. Most patients with NAFLD have few or no symptoms. However, in some cases, patients may complain of fatigue, malaise, and dull right-upper-quadrant abdominal discomfort. Mild jaundice may be noticed although this is rare. More commonly NAFLD is diagnosed following abnormal liver function tests during routine blood tests. By definition, alcohol consumption of over 20 g/day (about 25 ml/day) excludes the condition.

Furthermore, as discussed above circulating concentration above the Upper Limit of Normal (ULN) are suggestive of disease. Exemplary normal reference ranges are for GGT are 0-65 IU/L (adult males) and 0-45 IU/L (adult females), for ALT 6-63 IU/L (males) and 5-54 IU/L (females), for ALP 35-115 IU/L (both genders), for C3 0.92-2.10 mg/mL (both genders), wherein enzyme activity is expressed in international units (IU), the amount of enzyme that catalyzes the conversion of 1 µmole of substrate per minute and L is liters Additionally, a ratio between circulating activities of AST/ALT>2 is suggestive of Alcoholic liver disease (ALD) and <1 is indicative of NAFLD.

Thus, a combination of one or more of the known symptoms of ALD or NAFLD and elevated circulating activity/concentrations of liver enzymes is indicative of a person having ALD or NAFLD. Such an individual would benefit from treatment with limonin glucoside as disclosed herein.

Type 2 Diabetes

In addition to ALD and NAFLD, elevated circulating activity/concentrations of liver enzymes are also indicative of type 2 diabetes.

Other indicators of type 2 diabetes are well known in the art and include, but are not limited to: Frequent urination; Unusual thirst; Extreme hunger; Unusual weight loss; Extreme fatigue and Irritability; Frequent infections; Blurred vision; Cuts/bruises that are slow to heal; Tingling/numbness in the hands/feet; Recurring skin, gum, or bladder infections Thus, a combination of one or more of the known symptoms of type 2 diabetes and elevated circulating activity/concentrations of liver enzymes is indicative of a person having type 2 diabetes. Such an individual would benefit from treatment with limonin glucoside as disclosed herein.

Cardiovascular Disease (CVD)

In addition to ALD and NAFLD, and type 2 diabetes elevated circulating activity/concentrations of liver enzymes are also indicative of cardiovascular disease (CVD).

Other indicators of CVD include, but are not limited to: chest pain, shortness of breath, palpitations, weakness or dizziness, nausea, sweating.

Thus, a combination of one or more known symptoms of CVD and elevated circulating activity/concentrations of liver enzymes is indicative of a person having CVD. Such an individual would benefit from treatment with limonin glucoside as disclosed herein.

Chronic Kidney Disease (CKD)

In addition to conditions discussed above, elevated circulating activity/concentrations of liver enzymes are also indicative of chronic kidney disease.

Other indicators of chronic kidney disease (CKD) are well known in the art and include, but are not limited to night urination (nocturia); swelling of the legs and puffiness around the eyes (fluid retention); high blood pressure; fatigue and weakness (from anemia or accumulation of waste products in the body); loss of appetite, nausea and vomiting; itching, easy bruising, and pale skin (from anemia); shortness of breath from fluid accumulation in the lungs; headaches, numbness in the feet or hands (peripheral neuropathy), disturbed sleep, altered mental status (encephalopathy from the accumulation of waste products or uremic poisons), and restless legs syndrome; chest pain due to pericarditis (inflammation around the heart); bleeding (due to poor blood clotting); bone pain and fractures; decreased sexual interest and erectile dysfunction.

Thus, a combination of one or more known symptoms of CKD and elevated circulating activity/concentrations of liver enzymes is indicative of a person having CKD. Such an individual would benefit from treatment with limonin glucoside as disclosed herein.

Cancer

In addition to conditions discussed above, elevated circulating activity/concentrations of liver enzymes are also indicative of cancer.

There are many different kinds of cancers. Cancer can develop in almost any organ or tissue, such as the lung, colon, breast, skin, bones, or nerve tissue. That said, other indicators of cancer are well known in the art and include, but are not limited to e.g., lung cancer can cause coughing, shortness of breath, or chest pain. Colon cancer often causes diarrhea, constipation, and blood in the stool.

Thus, a combination of one or more known symptoms of cancer and elevated circulating activity/concentrations of liver enzymes is indicative of a person having cancer. Such an individual would benefit from treatment with limonin glucoside as disclosed herein.

Metabolic Syndrome

In addition to conditions discussed above, elevated circulating activity/concentrations of liver enzymes are also associated with metabolic syndrome.

Symptoms of metabolic syndrome are well known in the art (see e.g.,) and include, but are not limited to e.g., Fasting hyperglycemia, impaired fasting glucose, impaired glucose tolerance, or insulin resistance, high blood pressure, central obesity decreased HDL cholesterol, elevated triglycerides, etc.

A combination of one or more known symptoms of metabolic syndrome and elevated circulating activity/concentrations of liver enzymes is indicative of a person having metabolic syndrome. Such an individual would benefit from treatment with limonin glucoside as disclosed herein.

III. General Laboratory Procedures

When practicing the methods disclosed herein, a number of general laboratory tests can be used to assist in the diagnosis, progress and prognosis of the patient having a chronic disease associated with elevated levels of the liver enzymes gamma glutamyl transferase (GGT), alanine amino transferase (ALT), alkaline phosphatase (ALP) and complement fraction 3 (C3). Since elevations in these enzymes even within their normal ranges increase the incidences of Alcoholic Liver Disease (ALD), nonalcoholic fatty liver disease (NAFLD), metabolic syndrome (MS), type 2 diabetes (T2DM), chronic kidney disease (CKD), cardiovascular disease (CVD) and certain cancers, the methods disclosed herein, are used to assist in the diagnosis, progress, treatment and prognosis of the patient having Alcoholic Liver Disease (ALD), nonalcoholic fatty liver disease (NAFLD), type 2 diabetes, metabolic syndrome, chronic kidney disease (CKD), cardiovascular disease (CVD) and certain cancers. Different patients and disease conditions may require different dosage regimens and formulations. Such procedures and means to determine dosage regimens and formulations are well described in the scientific and patent literature. A few illustrative examples are set forth below.

III. Limonin Glucoside

Limonin glucoside is a liminoid compound. Limonoid compounds are highly oxygenated triterpenoid compounds found in tissues from members of the Rutaceae and Meliaceae plant families. For example, members of the Family Rutaceae, genus *Citrus* comprise limonoids in their juice, fruit tissues, and seeds.

Typically limonoid compounds are classified as belonging to one of five basic structural categories: (1) neutral aglycones e.g., limonin or nomilin; (2) monocarboxylic aglycones e.g., limonoic acid A-ring lactone; (3) dicarboxylic aglycones e.g., nomilinoic acid; (4) monocarboxylic glycosides e.g., limonin glucoside, and (5) dicarboxylic glycosides e.g., nomilinic acid glucoside (Herman Z., et al. (1992) In: *Modern Methods of Plant Analysis New Series*, Volume 14 Seed Analysis, Linskens, H. F. and Jackson, J. F. eds. Springer-Verlag Berlin, pgs 361-375).

An exemplary structural depiction of purified limonin glucoside is shown in FIG. 1.

A. Sources of Limonin Glucoside

Limonin glucoside is obtained from any synthetic method (see e.g., B. Heasley Eur. J. Org. Chem. 2011, 19-46) or any naturally occurring material comprising limonoid compounds. Typically, naturally occurring material comprising limonoid compounds fruits, peels, and seeds of plants from the Families Rutaceae and Meliaceae. For example, *citrus* fruit tissues and by-products of juice processing such as peels and molasses are ready sources of limonin gluco side.

Limonin glucoside containing material can be in any form, for example whole fresh fruit, whole dried fruit, particulate solid material, a liquefied suspension of solids and/or particulate solid dried extract obtained from *Citrus* species or species of genera closely related to *Citrus*; e.g., *citrus* seeds, processed *citrus* seed meal or extracts, filtrates or enzymatic digests of *citrus* seeds or *citrus* seed meal. In other embodiments the limonoid compound containing material is in the form of water soluble extracts, filtrates or enzymatic digests of limonoid compound containing material e.g., *citrus* fruit components, *citrus* juice processing by-products or processed *Citrus* including peel, pulp, core, seeds, juice, juice processing pulp wash, processed *Citrus* molasses and *citrus* fruit sections or obtained from species of genera closely related to *Citrus*. Purification of limonin glucoside is achieved using any method or combination of methods known in the art (see e.g., Breksa III, A. P., Manners, G. D., & Ibarra Jr., P. (2008). Journal of the Science of Food and Agriculture, 88: 2113-2218; Breksa III, A. P., Dragull, K., & Wong R Y (2008). Journal of Agricultural Food Chemistry, 56: 5595-5598; Breksa III, A. P., Hidalgo M B., & Wong R Y (2008). Stability of limonin glucoside In beverage matrices. Journal of the Science of Food and Agriculture 88: 2194-2200; Breksa III, A. P. & Dragull, K. (2009) Food Chemistry, 113:1308-1313; Breksa III, A. P., Hidalgo M B, Yuen M L (2009). Food Biochemistry 117: 739-744, etc.).

IV. Treating a Subject Having Elevated Levels of Liver Enzymes Using Limonin Glucoside Purified limonin glucoside is formulated as pharmaceuticals and/or nutraceuticals to be used in the methods disclosed herein to treat a subject having a chronic disease associated with elevated levels of the liver enzymes gamma glutamyl transferase (GGT), alanine amino transferase (ALT), alkaline phosphatase (ALP) and complement fraction 3 (C3). In some exemplary embodiments, treating a subject includes prophylactic administration. Elevations in liver enzymes even within normal ranges may increase the risk of incidences of Alcoholic Liver Disease (ALD), nonalcoholic fatty liver disease (NAFLD), type 2 diabetes, chronic kidney disease (CKD), cardiovascular disease (CVD) and certain cancers e.g., cervical, liver, prostate, lungs, digestive organs, lymphoid and hematopoietic cancers.

Routine means to determine limonin glucoside drug regimens and formulations to practice the methods of the invention are well described in the patent and scientific literature, and some illustrative examples are set forth below.

a. Determining Circulating Blood Concentration of Liver Enzymes

The invention may be practiced upon patients with apparently normal concentrations of circulating liver enzymes. Thus, in exemplary embodiments, the methods disclosed herein are practiced prophylactically. However, since the treatment for one or more of Alcoholic Liver Disease (ALD), Non-Alcoholic Fatty Liver Disease (NAFLD), type 2 diabetes, metabolic syndrome, cardiovascular disease, chronic kidney disease (CKD), and certain cancers, by administration of limonin glucoside includes reducing circulating concentrations of the liver enzymes gamma glutamyl transferase (GGT), alanine amino transferase (ALT), alkaline phosphatase (ALP) and complement fraction 3 (C3) in a subject, monitoring blood concentration of liver enzymes and determining baseline levels of liver enzymes are useful laboratory tests to aid in the diagnosis, treatment and prognosis of one or more of alcoholic Liver Disease (ALD), Non-Alcoholic Fatty Liver Disease (NAFLD), type 2 diabetes, cardiovascular disease, metabolic syndrome, chronic kidney disease (CKD), and certain cancers in a patient.

In one exemplary embodiment, a decrease from baseline levels of all four liver enzymes i.e., GGT, ALT, ADP and C3, following administration of limonin glucoside indicates limonin glucoside decreased production of these enzymes. Accordingly, limonin glucoside has caused an improvement in the disease condition e.g., improvement in the prognosis for recovery from a chronic disease selected from the group consisting of one or more of alcoholic Liver Disease (ALD), Non-Alcoholic Fatty Liver Disease (NAFLD), type 2 diabetes, cardiovascular disease, chronic kidney disease (CKD), and certain cancers. In another exemplary embodiment, a decrease from baseline levels of GGT and ALT, following administration of limonin glucoside to a subject in need thereof, indicates limonin glucoside decreased production of these enzyme and accordingly, has ameliorated the symptoms of elevated circulating concentrations of liver enzymes and caused an improvement in the disease condition e.g., improvement in the prognosis for recovery from a chronic disease selected from the group consisting of one or more of alcoholic Liver Disease (ALD), Non-Alcoholic Fatty Liver Disease (NAFLD), type 2 diabetes, cardiovascular disease, chronic kidney disease (CKD), and certain cancers.

A wide variety of laboratory tests exist that can be used to determine whether an individual has normal, low or high concentrations of circulating blood liver enzymes (see e.g. Yamada J, et al. Atherosclerosis. 2006 November; 189:198-205; Bo S, et al. World journal of gastroenterology: WJG. 2005 Dec. 7; 11:7109-17). Exemplary normal reference ranges are for GGT are 0-65 IU/L (adult males) and 0-45 IU/L (adult females), for ALT 6-63 IU/L (males) and 5-54 IU/L (females), for ALP 35-115 IU/L (both genders), for C3 0.92-2.10 mg/mL (both genders), wherein enzyme activity is expressed in international units (IU), the amount of enzyme that catalyzes the conversion of 1 μmole of substrate per minute and L is liters. Other commonly used ranges reported in literature are 0-30 IU/L for GGT, 30-40 IU/L for ALT and AST, 20-140 IU/L for ALP, and 0.75-1.35 mg/mL for C3 (Marshall M Kaplan 2012; Ruhl (2012) supra; Targher (2010) supra).

V. Limonin Glucoside as Pharmaceutical and Nutraceutical Compositions

Limonin glucoside used in the methods disclosed herein can be administered by any means known in the art, e.g., orally, parenterally, topically, or by local administration, such as e.g., transdermally. The methods disclosed herein provide for therapeutic treatments including prophylactic treatments. Limonin gluco side as a pharmaceutical or nutraceutical formulation can be administered in a variety of unit dosage forms depending upon whether the chronic disease associated with elevated liver enzymes e.g., NAFLD, is being treated after a subject has already acquired the disease, or if the subject is at risk of the disease but does not yet manifest symptoms of the disease (prophylactic administration), the general medical condition of each patient, the resulting preferred method of administration and the like. Details on techniques for formulation and administration are well described in the scientific and patent literature, see, e.g., the latest edition of Remington's Pharmaceutical Sciences, 17th ed. Edited by Alfonso R. Gennaro. Mack Publishing Co., 20th and Northampton Streets, Easton, Pa. ("Remington's"). A person of ordinary skill in the art will be able without undue experimentation, having regard to that skill and this disclosure, to determine a therapeutically effective amount of limonin glucoside for practice of the methods disclosed herein. For example, purified limonin glucoside may be more effective at higher or lower doses. By evaluating a patient using the methods disclosed herein, a skilled practitioner will be able to determine whether a patient is responding to treatment and will know how to adjust the dosage levels accordingly.

In general, limonin glucoside may be administered as pharmaceutical and/or nutraceutical compositions by any method known in the art for administering therapeutic drugs. Compositions may take the form of tablets, pills, capsules, semi-solids, powders, sustained release formulations, solutions, suspensions, elixirs, aerosols, or any other appropriate compositions; and comprise limonin glucoside in combination with at least one pharmaceutically acceptable excipient. Suitable excipients are well known to persons of ordinary skill in the art, and they, and the methods of formulating the compositions, may be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

Aqueous suspensions typically comprise limonin glucoside in admixture with excipients suitable for the manufacture of aqueous suspensions. Such excipients may include a suspending agent, such as e.g., sodium carboxymethylcellulose, methylcellulose, hydroxypropylmethylcellulose, sodium alginate, polyvinylpyrrolidone, gum tragacanth and gum *acacia*, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Therapeutically effective amounts purified limonin glucoside suitable for practice of the methods disclosed herein for adult human beings typically is in a range of between about 0.05 g/day to about 5.0 g/day. Thus, for a 70 Kg person, these doses will be 0.71-71 mg/Kg/day. Therapeutically effective doses of limonin glucoside are also used to treat children with elevated liver enzymes. Typically doses for children are smaller than for adults. Thus, typically for a 10 Kg child, a therapeutically effective dose of purified limonin glucoside is in a range that is between about 7.1 mg/day to about 71.4 mg/day or about 0.1 to about 10 mg/Kg/day. In one exemplary embodiment, a therapeutically effective dose is 0.5 g/day. In another exemplary embodiment, the dose is about 1 g/day. In still other exemplary embodiments the dose is 1.5 g/day, 2 g/day, 3 g/day, 4 g/day, 5 g/day, 6 g/day, 7 g/day, 8 g/day, 9 g/day, 10 g/day, 11 g/day, 12 g/day, 13 g/day, 14 g/day, 15 g/day, 16 g/day, 17 g/day, 18 g/day, 19 g/day. A person of ordinary skill in the art will be able without undue experimentation, having regard to that skill and this disclosure, to determine a therapeutically effective amount of a purified limonin glucoside for practice as disclosed herein.

Pharmaceutically acceptable carriers are determined in part by the particular composition being administered as well as by the particular method used to administer the composition. Accordingly, there are a wide variety of suitable formulations of pharmaceutical compositions of the present invention (see, e.g., Remington's supra).

For example, compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references Remington's supra. Suitable liquid carriers, especially for injectable solutions, include water, aqueous saline solution, aqueous dextrose solution, and glycols.

Aqueous suspensions of the invention contain purified limonin glucoside in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum *acacia*, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending purified limonin glucoside in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum *acacia* and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent Purified limonin glucoside pharmaceutical formulations can be prepared according to any method known to the art for the manufacture of pharmaceuticals. Such drugs can contain sweetening agents, flavoring agents, coloring agents and preserving agents. Any purified limonin glucoside formulation can be admixtured with nontoxic pharmaceutically acceptable excipients which are suitable for manufacture.

In another embodiment, the purified limonoid compound formulations of the invention are useful for intravenous (IV) administration. The formulations for administration will commonly comprise a solution of the limonin glucoside dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of purified limonin glucoside in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

After a pharmaceutical comprising a purified limonoid compound has been formulated in an acceptable carrier, it can be placed in an appropriate container and labeled for treatment of an indicated condition. For administration of purified limonin glucoside, such labeling would include, e.g., instructions concerning the amount, frequency and method of administration.

VI. Determining Dosing Regimens for Purified Limonin Glucoside

The methods of this invention treat chronic disease in a subject. The amount of purified limonin glucoside adequate to accomplish this is defined as a "therapeutically effective dose". The dosage schedule and amounts effective for this use, i.e., the "dosing regimen," will depend upon a variety of factors, including the severity of the disease, whether the treatment is being given after a subject is presenting with symptoms of a disease, or prophylactically, the patient's physical status, age, disease history, and the like. In calculating the dosage regimen for a patient, the mode of administration also is taken into consideration.

The dosage regimen also takes into consideration pharmacokinetics parameters well known in the art, e.g., the rate of absorption, bioavailability, metabolism, clearance, etc of the limonin glucoside (see, e.g., the latest Remington's, supra). The state of the art allows the clinician to determine the dosage regimen for each individual patient, and disease or condition treated. As an illustrative example, the guidelines provided below can be used as guidance to determine the dosage regiment of limonin glucoside, i.e., dose schedule and dosage levels, when practicing the methods disclosed herein.

Single or multiple administrations of purified limonin glucoside can be administered depending on the dosage and frequency as required and tolerated by the patient. The formulations should provide a sufficient quantity of active agent, i.e., limonin glucoside, to effectively treat one or more of alcoholic Liver Disease (ALD), Non-Alcoholic Fatty Liver Disease (NAFLD), type 2 diabetes, metabolic syndrome, cardiovascular disease, chronic kidney disease (CKD), and certain cancers, in a subject. Thus, exemplary pharmaceutical formulation for oral administration of limonin glucoside by adults is in a daily amount that is in a range that is between about 0.05 g/day to about 5.0 g/day (0.71-71 mg/Kg/day) and for children 7.1 mg/day to about 71.4 mg/day (0.1-10 mg/Kg/day). Lower dosages can be used, particularly when the drug is administered into the blood stream, into a body cavity or into a lumen of an organ as opposed to administration orally. Substantially higher dosages can be used in topical administration. Actual methods for preparing parenterally administrable limonin glucoside formulations will be known or apparent to those skilled in the art and are described in more detail in such publications as Remington's, supra.

After a pharmaceutical comprising limonin glucoside has been formulated in an acceptable carrier, it can be placed in an appropriate container and labeled for treatment of an indicated condition. For administration of purified limonin glucoside, such labeling would include, e.g., instructions concerning the amount, frequency and method of administration. In one embodiment, the invention provides for a kit for treating, including prophylactic treatment, of one or more of alcoholic Liver Disease (ALD), Non-Alcoholic Fatty Liver Disease (NAFLD), type 2 diabetes, cardiovascular disease, chronic kidney disease (CKD), and certain cancers in a subject which includes purified limonin glucoside composition and instructional material teaching the indications, dosage and schedule of administration of the purified limonin glucoside.

EXAMPLES

Example 1

The following example illustrates that administration of limonin glucoside to a subject in need thereof, is effective for reducing the circulating blood concentrations of liver enzymes GGT, ALT, ALP and C3.

List of Abbreviations:

ALP, alkaline phosphatase; ALT, alanine amino transferase; AST, aspartate amino transferase; C3, complement fraction 3; CBC, complete blood cell count; CKD, chronic kidney disease; CMP, comprehensive metabolic panel; CKMB, creatinine kinase MB; CRP, C reactive protein; CVD, cardiovascular disease; EGF, epidermal growth factor; GGT, gamma glutamyl transferase; IL, interleukin; Il-1Ra, interleukin-1 receptor antagonist; LG, limonin glucoside; LPS, lipopolysaccharide; MAP 1.6, multi-analyte panel 1.6; NAFLD, nonalcoholic fatty liver disease; PBMNC, peripheral blood mononuclear cells; PSA, prostate specific antigen; SSA, serum amyloid A; sICAM-1, soluble intracellular adhesion molecule-1; sVCAM-1, soluble vascular cell adhesion molecule-1; T2DM, type 2 diabetes mellitus; TNF α, tumor necrosis factor α; WHNRC, Western Human Nutrition Research Center Materials and Methods for Example 1

Complete Blood Cell Count

Complete and differential cell counts were performed at the hematology laboratory of University of California Medical Center (UCDMC), Sacramento using Beckman Coulter LH 700.

Comprehensive Metabolic Panel (CMP), Gamma Glutamyl Transferase (GGT), and Creatinine Kinase MB (CKMB)

CMP performed on serum samples at the chemistry laboratory of University of California Medical Center by using the Beckman Coulter DxC800. GGT and CKMB were determined in the EDTA plasma. GGT activity was determined by using Integra 400 Chemistry Analyzer, Roche Diagnostics. CKMB concentration was determined by using the Multiplex kits from Mesoscale Discovery (Gaithersburg, Md. 20877).

Serum Lipids and Lipoproteins

Serum lipids were part of the CMP performed at University of California Medical Center (UCDMC) by using the Beckman Coulter DxC800 instrument. Lipoproteins A1 and B were ascertained in EDTA plasma using a Cobas Integra 400 Plus instrument with Roche reagents (Roche Diagnostics Corp., Indianapolis, Ind.). Lipoproteins C2, C3 and E were quantified in serum using a Cobas Integra 400 Plus instrument with Kamiya reagents (Kamiya Biomedical Co., Seattle, Wash.).

Lipoprotein Size and Sub Fraction Concentrations

Mean particle size, total number of particles and their number within different subclasses of VLDL, LDL, and HDL, were determined by NMR methods. For this analysis frozen plasma samples were shipped in dry ice by overnight delivery to LipoScience Inc., who performed the analysis.

Serum/Plasma Concentrations of Inflammatory Markers

Plasma concentrations of epidermal growth factor (EGF), interleukin-13 (IL-13), interleukin-1 receptor antagonist (IL-1Ra), and tumor necrosis factor α (TNF α) were analyzed in EDTA plasma on a Sector Imager 2400 instrument using a multiplex kits from MSD (Meso-Scale Discovery, Gaithersburg, Md.). Concentrations of C reactive protein (CRP), and complement 3 and 4 (C3, C4) were analyzed in serum by using an Integra 400 Plus Chemistry Analyzer, (Roche Diagnostics Corp., Indianapolis, Ind.). Serum amyloid A (SAA), soluble intracellular adhesion molecule-1 (sICAM-1), and soluble vascular cell adhesion molecule-1 (sVCAM-1) were tested in serum on a Sector Imager 2400 instrument using a multiplex kit from MSD (Meso-Scale Discovery, Gaithersburg, Md.).

Ex-Vivo Production of Cytokines

Peripheral blood mononuclear cells (PBMNC) were isolated by using Dulbecco's phosphate buffered saline (DPBS) and suspended in Russ's-10 medium containing 10% autologous sera at concentrations of 1 million/mL. PBMNC were cultured in Costar 96-well sterile flat bottom plates coated with mouse anti-human CD3 and CD28 to stimulate T cells. Another set of wells were stimulated with LPS (final concentration 10 ng/mL) to stimulate monocytes. Cell culture supernatants were collected at 24, 48, and 72 hr after stimulation by centrifugation. Cell culture supernatants were stored at −80° C. until tested for cytokine concentrations. All cytokines were analyzed on a BioPlex instrument (BioRad Laboratories, Richmond, Calif.) with multiplex reagents kits (Millipore Corp., Danvers, Mass.).

MYRIAD Rules Based Medicine (RBM) Multi-Analyte Panel (MAP1.6)

Plasma samples prepared from blood collected in EDTA-containing tubes were stored at −80° C. until tested. The samples were thawed at room temperature, vortexed, spun at 13,000×g for 5 minutes for clarification and 100 uL aliquots were removed for MAP analysis into a master microtiter plate. Using automated pipetting, an aliquot of each sample was introduced into one of the capture microsphere multiplexes of the Human MAP 1.6. This MAP comprised of 89 antigens that included markers for oxidative stress, inflammation, immune status, T2DM, CVD, blood clotting, cancer, liver and kidney functions. All plasma samples were tested in duplicate. The mixture of sample and capture microspheres were thoroughly mixed and incubated at room temperature for 1 hour. Multiplexed cocktails of biotinylated, reporter antibodies for each multiplex were then added robotically and after thorough mixing, were incubated for an additional hour at room temperature. Multiplexes were developed using an excess of streptavidin-phycoerythrin solution which was thoroughly mixed into each multiplex and incubated for 1 hour at room temperature. The volume of each multiplexed reaction was reduced by vacuum filtration and the volume increased by dilution into matrix buffer for analysis. Analysis was performed in a Luminex 100 instrument and the resulting data stream was interpreted using proprietary data analysis software developed at Rules-Based Medicine. For each multiplex, both calibrators and controls were included on each microtiter plate. 8-point calibrators were run in the first and last column of each plate and 3-level controls were included in duplicate. Testing results were determined first for the high, medium and low controls for each multiplex to ensure proper assay performance. Unknown values for each of the analytes localized in a specific multiplex were determined using 4 and 5 parameter, weighted and non-weighted curve fitting algorithms included in the data analysis package. The intra-sample coefficient of variance (CV) for all antigens with concentrations above the lowest detectable dose (LDD) was less than 20%, and was less than 10% for more than 50% of the antigens tested.

Statistical Analysis

SAS PROC MIXED was used to fit the cross-over model (Littell R C, Milliken G A, Stroup W W, Wolfinger R D, Schabenberger O. SAS System for Mixed Models. Cay, N.C.: SAS Institute Inc.; 2006). Transformations were used when appropriate to stabilize the variances among the diets and periods. The fixed effects were order, diet, the interaction and the covariate; and the random effect was subjects within order. The test for order is a test for carry-over effect. Since there was generally no evidence of a carry-over effect, data from the two cohorts were pooled. Comparisons were made between the values at the end of placebo and LG treatments and using the baseline data as a covariate. Results are presented as means±SEM. Differences were considered statistically significant for P value<0.05.

Results for Example 1

Limonin Glucoside Purification

Limonin Glucoside (LG) was obtained from a combination of sources including clarified frozen orange juice by methods known in the art (see e.g., Breksa et al., (2008) Journal of the Science of Food and Agriculture, 88: 2113-2218; Breksa III, A. P., et al., (2008). Journal of the Science of Food and Agriculture 88: 2194-2200; Breksa A. P., et al., (2008) Journal of Agricultural Food Chemistry, 56: 5595-5598; Breksa & Dragull, (2009) Food Chemistry, 113:1308-1313; Breksa III, A. P., et al., (2009). Food Biochemistry 117: 739-744), and also from *citrus* molasses and *citrus* molasses extracts using methods known in the art (see e.g., Schoch T. K. et al. (2002) Journal Food Science 67:3159-3163). The resulting material was further purified by recrystallization from water. A final polishing of the crystallized material by C-18 flash chromatography (Breksa & Dragull, (2009), supra) yielded limonin glucoside in a purity in excess of 99.93%. 475 grams of material was isolated using this process.

Pre-Study Characteristics of Subjects

Five overweight and obese men and five women participated in the study. They ranged 24-59 years in age and 24.8-31.8 Kg/m$^2$ in BMI. Mean pre-study values for their age, BMI, blood lipids, glucose, and blood pressure are given in Table 1. With the exception of total and LDL-cholesterol, all other blood parameters were within the normal ranges.

TABLE 1

Pre-study anthropometric and metabolic characteristics of study participants(5 men + 5 women)

| Variable | Mean ± SEM (n = 10) |
|---|---|
| Age, Y | 47.6 ± 3.8 |
| BMI, Kg/m$^2$ | 28.3 ± 0.7 |
| Serum glucose, mg/dL | 86.3 ± 2.4 |
| Serum triglycerides, mg/dL | 146.7 ± 17.6 |
| Serum total cholesterol, mg/dL | 236.3 ± 8.1 |
| Serum HDL-C, mg/dL | 86.3 ± 2.4 |
| Serum LDL-C, mg/dL | 162.0 ± 7.9 |
| Serum protein, g/dL | 6.8 ± 0.1 |

TABLE 1-continued

Pre-study anthropometric and metabolic characteristics of study participants(5 men + 5 women)

| Variable | Mean ± SEM (n = 10) |
|---|---|
| Systolic BP, mm Hg | 115.8 ± 8.0 |
| Diastolic BP, mm Hg | 69.3 ± 3.7 |
| Heart rate, BPM | 66.3 ± 2.6 |

Blood parameters refer to 12-hr fasting values. Abbreviations are: BP, blood pressure; BMI, body mass index; BPM, beats per minute Adverse Effects of the LG and Placebo Drinks A total of 11 adverse events were reported by 6 subjects for the entire duration of the study (data not shown). Some of these events such as volunteer hurting her back or hand were definitely unrelated to the drinks, while others like a weird taste, dry throat seem related to the drinks, still others such as mild cold or frequent urinating, or rash on chest may or may not be related to the drinks. Overall, the drinks were well tolerated and only mild adverse effects were reported. At the time those adverse events were reported, both the volunteers and the investigators were blinded to the drinks, hence it could not be determined if the effect was specific to LG. A subsequent review of these events after the subject's code was known showed that 7 out of the 11 adverse events were reported when the subjects were taking placebo drinks and 4 when they were taking the LG drink. Since the placebo was also the carrier of LG, all adverse events may be due to the placebo drinks.

Compliance with the Drinks

Subjects picked drinks every two weeks from Western Human Nutritional Research Center (WHNRC) and they were asked to return any unused drinks at the time of each pick up. None of the drinks were returned, indicating 100% compliance. Subjects were also provided diaries to list any adverse events and the time of the day when they consumed their study drinks. Only 6 out of 10 subjects returned those diaries at the end of the study. Four of those had completed 100% entries for drinks consumed, one completed 95%, and one completed only 11%. The fact none of drinks were returned suggests that the overall compliance was better than 90% even if some of subjects did not return their diaries.

Effect of Limonin Glucoside on Hematological Parameters

LG drink did not alter any of the hematological variables when compared to their corresponding values at the end of placebo treatment and using baseline data as covariates (Table 2).

TABLE 2

Effect of limoninglucoside (LG) supplementation on hematological parameters in human subjects

| Variable | End baseline | End Placebo | End LG |
|---|---|---|---|
| WBC, # × $10^{-9}$/L | 5.96 ± 0.49 | 5.48 ± 0.31 | 5.55 ± 0.38 |
| Neutrophils, # × $10^{-9}$/L | 3.84 ± 0.35 | 3.18 ± 0.25 | 3.14 ± 0.30 |
| % of WBC | 61.34 ± 1.91 | 57.81 ± 2.64 | 55.41 ± 3.16 |
| Lymphocytes, # × $10^{-9}$/L | 1.81 ± 0.12 | 1.73 ± 0.15 | 1.80 ± 0.14 |
| % of WBC | 29.00 ± 1.72 | 31.58 ± 2.05 | 33.01 ± 2.09 |
| Monocytes, # × $10^{-9}$/L | 0.39 ± 0.03 | 0.36 ± 0.03 | 0.42 ± 0.03 |
| % of WBC | 6.11 ± 0.40 | 6.92 ± 0.54 | 7.79 ± 1.03 |
| Eosinophil, # × $10^{-9}$/L | 0.19 ± 0.05 | 0.19 ± 0.03 | 0.18 ± 0.03 |
| % of WBC | 2.90 ± 0.64 | 3.25 ± 0.56 | 3.32 ± 0.52 |
| Basophils, # × $10^{-9}$/L, | 0.04 ± 0.00 | 0.03 ± 0.00 | 0.03 ± 0.00 |
| % of WBC | 0.64 ± 0.20 | 0.44 ± 0.07 | 0.47 ± 0.04 |
| Platelets, # × $10^{-9}$/L | 249.55 ± 13.64 | 229.20 ± 12.70 | 229.00 ± 12.74 |
| RBC, # × $10^{-12}$/L | 4.61 ± 0.13 | 4.59 ± 0.11 | 4.54 ± 0.13 |

TABLE 2-continued

Effect of limoninglucoside (LG) supplementation on hematological parameters in human subjects

| Variable | End baseline | End Placebo | End LG |
|---|---|---|---|
| Hematocrit, % | 42.01 ± 1.03 | 41.67 ± 0.93 | 41.47 ± 1.00 |
| Hemoglobin, g/dL | 14.22 ± 0.34 | 14.26 ± 0.49 | 13.94 ± 0.61 |
| MCH, pico grams | 30.91 ± 0.44 | 31.04 ± 0.37 | 31.08 ± 0.39 |
| MCV, microns | 91.26 ± 1.08 | 90.93 ± 1.08 | 91.44 ± 1.29 |
| MCHC, % | 33.85 ± 0.18 | 34.14 ± 0.14 | 33.98 ± 0.16 |
| RDW, % | 12.97 ± 0.18 | 13.02 ± 0.19 | 13.12 ± 0.13 |
| pH | 6.30 ± 0.25 | 6.45 ± 0.34 | 6.75 ± 0.27 |
| Specific gravity | 1.02 ± 0.00 | 1.02 ± 0.00 | 1.02 ± 0.00 |

Data are Mean ± SEM (n = 10). Abbreviations are: MCH, Mean corpuscular hemoglobin; MCV, Mean corpuscular volume; MCHC, Mean corpuscular hemoglobin concentration; RBC, red blood cells; RDW, red cell distribution width; WBC, white blood cells. This was a cross-over study and all subjects received both the placebo and LG drinks for 56 days each, and there was an initial baseline period of 14 days with placebo drinks. There was no evidence of carry- over effect; hence data from the two groups were pooled. None of the variables were significantly different between ends of placebo and LG treatments as tested by SAS mixed models and using baseline data as the covariate.

Effect of Limonin Glucoside on the Concentrations of Markers for Metabolic Comprehensive Panel, Cretinine Kinase MB (CKMB) and Gamma Glutamyl Transferase (GGT)

LG treatment did not alter the concentrations of serum albumin, total protein, glucose, aspartate amino transferase, lactate dehydrogenase, calcium, potassium, sodium, chloride, $CO_2$, creatinine, CKMB, total bilirubin, and urea when compared with the corresponding values at the end of placebo treatment (Table 3). LG treatment decreased the plasma activity of Gamma glutamyl transferase (GGT) by 33.8% (p=0.001), that of serum alanine aminotransferase (ALT) by 13.1% (p=0.041), and that of serum alkaline phosphatase (ALP) by 10.1% (p=0.025) when compared with corresponding values at the end of placebo treatment.

TABLE 3

Effect of limonin glucoside (LG) supplementation on the activity/concentration of markersin serum/plasma samples

| Variable | End baseline | End placebo | End LG |
|---|---|---|---|
| Albumin, g/dL | 3.98 ± 0.07 | 3.94 ± 0.06 | 3.95 ± 0.05 |
| Protein, g/dL | 6.66 ± 0.11 | 6.62 ± 0.09 | 6.59 ± 0.08 |
| Glucose, mg/dL | 84.80 ± 2.35 | 86.40 ± 1.94 | 89.7 ± 2.58 |
| Alkaline phosphatase, U/L | 66.9 ± 04.93 | 66.20 ± 5.08 | 59.5 ± 3.47* |
| Alanine amino trasferase, U/L | 26.50 ± 2.77 | 29.00 ± 5.01 | 25.2 ± 5.08* |
| Aspartate amino transferase, U/L | 24.30 ± 2.11 | 25.00 ± 2.33 | 23.3 ± 2.22 |
| Calcium, mg/dL | 9.45 ± 0.08 | 9.38 ± 0.07 | 9.42 ± 0.06 |
| Potassium, mEq/L | 4.39 ± 0.10 | 4.50 ± 0.08 | 4.61 ± 0.12 |
| Sodium, mEq/L | 139.2 ± 0.68 | 139.5 ± 0.73 | 140.80 ± 0.68 |
| Chloride, mEq/L | 103.70 ± 0.82 | 103.20 ± 0.53 | 104.80 ± 0.81 |
| $CO_2$, mEq/L | 29.80 ± 0.47 | 28.10 ± 0.46 | 29.10 ± 0.48 |
| Creatinine, mg/dL | 0.89 ± 0.05 | 0.87 ± 0.03 | 0.84 ± 0.03 |
| Total bilirubin, mg/dL | 0.94 ± 0.09 | 0.87 ± 0.08 | 0.81 ± 0.08 |
| Urea, mg/dL | 12.30 ± 0.72 | 12.30 ± 0.88 | 11.70 ± 0.92 |
| Lactate dehydrogenase, (U/L) | 138.70 ± 6.70 | 134.60 ± 9.00 | 126.80 ± 8.90 |
| CKMB, ng/mL | 2.53 ± 0.51 | 3.92 ± 1.12 | 2.60 ± 0.50 |
| GGT, (U/L) | 32.4 ± 8.6 | 38.0 ± 13.1 | 25.2 ± 8.0* |

Data are Mean ± SEM (n = 10). Abbreviations are: GGT, Gamma glutamyl transferase; CKMB, creatinine kinase MB. Numbers bearing an * are significantly different between the placebo and LG groups (p < 0.05) using SAS mixed model procedures and baseline data as the covariate. For other details see legend for table 2 and methods section.

Effect of Limonin Glucoside Supplementation on Serum Concentrations of Lipids and Lipoproteins LG supplementation did not alter serum concentrations of total-, HDL-, LDL-, and non-HDL-cholesterol, triglycerides, lipoproteins A1, B, C2, C3, and E when compared with corresponding values at the end of placebo treatment (Table 4).

TABLE 4

Effect of limonin glucoside (LG) supplementation on serum concentrations of lipids and lipoproteins

| Variable | End baseline | End placebo | End LG |
| --- | --- | --- | --- |
| Cholesterol, mg/dL | 230.40 ± 7.19 | 236.2 ± 10.51 | 231.70 ± 8.83 |
| HDL-C, mg/dL | 44.70 ± 4.23 | 46.2 ± 2.55 | 44.20 ± 2.59 |
| LDL-C (Calc), mg/dL | 158.50 ± 6.64 | 160.90 ± 10.23 | 159.10 ± 7.37 |
| Non-HDL-C, mg/dL | 185.70 ± 9.08 | 190.00 ± 11.60 | 187.50 ± 10.63 |
| Total-C:HDL-C | 5.58 ± 0.54 | 5.28 ± 0.42 | 5.47 ± 0.47 |
| Triglycerides, mg/dL | 135.50 ± 17.46 | 145.70 ± 24.42 | 142.60 ± 23.64 |
| Lipoprotein A1, mg/dL | 142.52 ± 5.56 | 144.06 ± 4.80 | 142.91 ± 4.18 |
| Lipoprotein B, mg/dL | 113.4 ± 6.85 | 113.5 ± 7.26 | 114.5 ± 6.45 |
| Lipoprotein C2, mg/dL | 6.37 ± 0.57 | 6.37 ± 0.58 | 6.21 ± 0.50 |
| Lipoprotein C3, mg/dL | 13.71 ± 0.99 | 13.98 ± 1.58 | 13.28 ± 1.05 |
| Lipoprotein E, mg/dL | 4.89 ± 0.26 | 5.21 ± 0.42 | 4.91 ± 0.32 |

Data are Mean ± SEM (n = 10). None of the variables were significantly different between ends of placebo and LG treatments as tested by SAS mixed models and using baseline data as the covariate. For other details see legend for table 2 and methods section.

LG supplementation also did not alter the mean particle sizes for VLDL, LDL, and HDL particles, concentrations of large, medium, and small sub-fractions in each particle type, and cholesterol concentrations in different sub-fractions (Table 5).

Effect of Limonin Glucoside Supplementation on Markers of Inflammation

Plasma concentrations of EGF, IL-13, IL-1Ra, and TNF α, and serum concentrations of CRP, SAA, sICAM-1, sVCAM-1), and C4 were not altered by LG supplementation when compared with the corresponding values at the end of placebo treatment (Table 6). LG supplementation decreased serum C3 concentration by 4.8% when compared to the corresponding values following placebo treatment (p=0.055).

TABLE 6

Effect of limonin glucoside (LG) supplementation on serum/plasma concentrations of markers of inflammation.

| Variable | End baseline | End placebo | End LG |
| --- | --- | --- | --- |
| EGF, pg/mL | 141.37 ± 92.45 | 89.57 ± 22.02 | 106.02 ± 52.55 |
| IL-13, pg/mL | 2.91 ± 0.79 | 2.03 ± 0.47 | 2.42 ± 0.27 |
| IL-1Ra, pg/mL | 190.53 ± 15.0 | 217.86 ± 44.55 | 194.93 ± 27.03 |
| TNF a, pg/mL | 0.74 ± 0.18 | 0.71 ± 0.35 | 0.58 ± 0.20 |
| CRP, μg/mL | 1.73 ± 0.37 | 1.81 ± 0.29 | 1.64 ± 0.25 |
| SAA, μg/mL | 4.56 ± 1.09 | 4.47 ± 0.78 | 4.06 ± 0.77 |
| C3, mg/mL | 1.27 ± 0.08 | 1.24 ± 0.06 | 1.18 ± 0.05* |
| C4, mg/mL | 0.32 ± 0.01 | 0.31 ± 0.02 | 0.29 ± 0.02 |
| sICAM-1, μg/mL | 0.25 ± 0.02 | 0.25 ± 0.02 | 0.25 ± 0.02 |
| sVCAM-1, μg/mL | 0.38 ± 0.04 | 0.41 ± 0.04 | 0.41 ± 0.04 |

Data are Mean ± SEM (n = 10). Abbreviations are: EGF, epidermal growth factor; IL, interleukin; IL-Ra, IL-receptor antagonist; CRP, C-reactive protein; SAA, serum amyloid A; C3, complement fraction C3; C4, complement fraction C4, sICAM-1, soluble intracellular adhesion molecule-1; sVCAM-1, soluble vascular cell adhesion molecule-1. Numbers bearing an * are significantly different between the placebo and LG groups (p < 0.05) using SAS mixed model procedures and baseline data as the covariate. For other details see legend for table 2 and methods section.

TABLE 5

Effect of limonin glucoside(LG) supplementation on the concentration and size of plasma lipoprotein particles

| Variable | End baseline | End placebo | End LG |
| --- | --- | --- | --- |
| Total VLDL & chylomicron particles, nmol/L | 90.03 ± 13.56 | 83.70 ± 13.26 | 86.69 ± 13.15 |
| Large VLDL & chylomicron particles, nmol/L | 2.61 ± 0.83 | 4.00 ± 1.45 | 3.50 ± 1.64 |
| Medium VLDL & chylomicron particles, nmol/L | 38.38 ± 8.99 | 36.14 ± 9.46 | 37.70 ± 8.22 |
| Small VLDL & chylomicron particles, nmol/L | 49.05 ± 5.92 | 43.53 ± 4.15 | 45.47 ± 5.95 |
| Mean particle size, nm | 47.33 ± 2.40 | 50.67 ± 2.69 | 48.60 ± 2.25 |
| Total LDL particle, nmols/L | 1472.80 ± 111.43 | 1514.90 ± 112.66 | 1582.80 ± 118.15 |
| IDL particles, nmols/L | 57.10 ± 14.21 | 61.20 ± 16.26 | 71.80 ± 14.77 |
| Large LDL particles, nmols/L | 480.80 ± 71.92 | 492.10 ± 87.03 | 495.80 ± 71.47 |
| Total small LDL particles, nmols/L | 934.70 ± 155.26 | 961.70 ± 167.71 | 1015.20 ± 169.46 |
| Medium small LDL particles, nmols/L | 185.00 ± 29.76 | 203.40 ± 37.86 | 208.40 ± 35.06 |
| Very small LDL particles, nmols/L | 749.60 ± 126.12 | 758.40 ± 130.33 | 806.80 ± 134.82 |
| Mean particle size, nm | 20.97 ± 0.28 | 20.99 ± 0.299 | 20.94 ± 0.26 |
| Total HDL particles, μmols/L | 31.42 ± 1.06 | 32.45 ± 1.45 | 31.35 ± 0.95 |
| Large HDL particles, μmols/L | 6.95 ± 1.25 | 6.50 ± 1.07 | 6.57 ± 0.99 |
| Medium HDL particles, μmols/L | 3.22 ± 0.86 | 4.53 ± 1.38 | 4.54 ± 1.43 |
| Small HDL particles, μmols/L | 21.23 ± 1.60 | 21.44 ± 2.48 | 20.25 ± 1.94 |
| Mean particle size, nm | 8.89 ± 0.14 | 8.87 ± 0.12 | 8.86 ± 0.12 |
| VLDL & chylomicron total TG, mg/dL | 100.90 ± 17.96 | 108.50 ± 24.17 | 106.50 ± 22.20 |
| Large VLDL & chylomicron TG, mg/dL | 25.99 ± 6.97 | 37.46 ± 11.48 | 33.01 ± 13.18 |
| Medium VLDL TG, mg/dL | 52.88 ± 13.06 | 51.49 ± 14.51 | 53.08 ± 11.93 |
| Small VLDL TG, mg/dL | 22.05 ± 2.63 | 19.46 ± 1.84 | 20.32 ± 2.64 |
| LDL total cholesterol, mg/dL | 128.60 ± 5.25 | 133.10 ± 6.18 | 137.60 ± 5.14 |
| IDL cholesterol, mg/dL | 7.10 ± 1.76 | 7.58 ± 2.01 | 8.93 ± 1.83 |
| Large LDL cholesterol, mg/dL | 65.46 ± 9.93 | 66.68 ± 11.84 | 67.24 ± 9.75 |
| Small LDL cholesterol, mg/dL | 56.01 ± 9.27 | 58.68 ± 10.46 | 61.47 ± 10.32 |
| Medium small LDL cholesterol, mg/dL | 20.03 ± 3.21 | 22.05 ± 4.13 | 22.60 ± 3.80 |
| Very small LDL cholesterol, mg/dL | 36.01 ± 6.11 | 36.63 ± 6.37 | 38.91 ± 6.55 |
| HDL cholesterol total, mg/dL | 46.90 ± 3.36 | 47.60 ± 3.06 | 46.10 ± 2.65 |
| Large HDL cholesterol, mg/dL | 21.78 ± 4.22 | 20.43 ± 3.53 | 20.19 ± 3.24 |
| Medium HDL cholesterol, mg/dL | 4.18 ± 3.49 | 5.84 ± 1.79 | 5.87 ± 1.87 |
| Small HDL cholesterol, mg/dL | 21.05 ± 1.59 | 21.25 ± 2.45 | 20.03 ± 1.91 |
| Calculated TG total, mg/dL | 141.80 ± 19.09 | 150.60 ± 24.48 | 150.50 ± 22.84 |
| Calculated cholesterol total, mg/dL | 200.80 ± 5.23 | 204.70 ± 6.40 | 208.50 ± 5.45 |

Data are mean ± SEM (n = 10). Lipoprotein particle size and concentrations were determined by using NMR. There was no evidence of carry-over effect; hence the data from the two groups were pooled. None of the variables were significantly different between ends of placebo and LG treatments as tested by SAS mixed models and using baseline data as the covariate. For other details see legend for table 2 and methods section.

Ex-vivo secretion of cytokines produced by T cells stimulated with CD3/28 (IFN γ, TNF α, IL-4, IL-2, and IL-10) for 72 hr. did not differ between the LG and placebo treatments (Table 7). Nor did the secretion of IL-6, IL-1β, and TNF cc by monocytes stimulated by LPS for 24 hr, differ between the two treatments. Although not significant, concentrations of all secreted cytokines except IL-10 were lower after the LG treatment group (8-18%), than the corresponding values following the placebo treatment (Table 7). Lack of significance may be due to the small number of subjects in the study and the large variances among the subjects.

TABLE 7

Effect of limoninglucoside (LG) supplementation on the ex vivo production of cytokines by peripheral blood mononuclear cells.

| Variable | End baseline | End placebo | End LG |
|---|---|---|---|
| [1]Interferon γ, pg/mL | 491650 ± 11759 | 59497 ± 10362 | 51700 ± 10536 |
| [1]TNF α, pg/mL | 6271 ± 1151 | 7498 ± 1264 | 6723 ± 970 |
| [1]IL-4, pg/mL | 61.9 ± 15.6 | 81.3 ± 20.1 | 66.7 ± 12.8 |
| [1]IL-2, pg/mL | 110.1 ± 57.6 | 104.8 ± 53.6 | 58.8 ± 25.8 |
| [1]IL-10, pg/mL | 546.4 ± 110.6 | 759.4 ± 96.4 | 779 ± 126 |
| [2]IL-6, pg/mL | 7669 ± 2356 | 11911 ± 1818 | 10926 ± 1586 |
| [2]TNF α, pg/mL | 1106 ± 367 | 1473 ± 251 | 1354 ± 231 |
| [2]IL-1β, pg/mL | 5233 ± 2274 | 5154 ± 1124 | 4731 ± 1123 |

[1]Cells stimulated with CD3/28 (each 0.75 μg/mL, 72 hr); [2]cells stimulated with LPS (10 ng/mL, 24 hr). Data are Mean ± SEM (n = 10). Abbreviations are: IL, interleukin; TNF, tumor necrosis factor. None of the variables were significantly different between ends of placebo and LG treatments as tested by SAS mixed models and using baseline data as the covariate. For other details see legend for table 2 and methods section.

Effect of LG Supplementation on Plasma Concentrations of Biomarkers for Human Chronic Diseases (Rules Based Medicine Human Multiple Analyte Panel 1.6)

Out of the 89 biomarkers tested, concentrations of 74 were above the lowest detection dose (LDD) while those of 15 were lower than the LDD (Table 8). Concentration of C3 was significantly lower after LG treatment when compared with the concentration at the end of placebo treatment (6.4%, p=0.014). This decrease in C3 confirms the decrease observed by the analysis of C3 by Integra 400 Plus Chemistry Analyzer (4.8%, p=0.055, Table 6). Similarly the concentration of free prostate specific antigen (PSA) was 13.9% lower following the LG treatment as compared with its concentration following placebo treatment (p=0.053). Plasma free PSA concentration was 10-20 folds greater in males than in females (not shown). Free PSA concentration was reduced by LG in all 5 men and 3 women. If the data for men and women were analyzed separately, there was a 14.5% decrease caused by LG in men (p=0.059, n=5) and 22.9% in women (p=0.309, n=5). Very low concentration of PSA, large variance, and a small n, made the change in plasma free PSA in women non-significant. Besides PSA and C3, tumor necrosis factor α (p=0.085), matrix metalloproteinase-9 (p=0.118) and serum amyloid P (p=0.188) showed trends for decrease with LG supplementation.

TABLE 8

Effect of limonin glucoside (LG) supplementation on plasma concentrations of biomarkers for human chronic diseases (Rules Based Medicine human multiple analyte panel 1.6).

| Variable | End baseline | End placebo | End LG |
|---|---|---|---|
| Alpha-1 Antitrypsin, mg/mL | 2.21 ± 0.13 | 2.09 ± 0.11 | 2.19 ± 0.10 |
| Adiponectin, μg/mL | 3.10 ± 0.69 | 3.44 ± 0.74 | 3.19 ± 0.70 |
| Alpha-2 Macroglobulin, mg/mL | 0.84 ± 0.08 | 0.82 ± 0.07 | 0.79 ± 0.06 |
| Alpha-Fetoprotein, ng/mL | 2.42 ± 0.21 | 2.58 ± 0.27 | 2.35 ± 0.19 |
| Apolipoprotein A1, mg/mL | 0.32 ± 0.03 | 0.28 ± 0.02 | 0.30 ± 0.01 |
| Apolipoprotein CIII, μg/mL | 117.00 ± 8.40 | 102.18 ± 14.46 | 111.60 ± 12.92 |
| Apolipoprotein H, μg/mL | 261.85 ± 18.70 | 254.65 ± 17.74 | 257.10 ± 19.26 |
| Beta-2 Microglobulin, μg/mL | 1.52 ± 0.16 | 1.52 ± 0.16 | 1.46 ± 0.14 |
| Brain-Derived Neurotrophic Factor, ng/mL | 6.29 ± 1.99 | 3.00 ± 0.63 | 2.88 ± 0.71 |
| Complement 3, mg/mL | 1.23 ± 0.07 | 1.25 ± 0.05 | 1.17 ± 0.05* |
| CD 40, ng/mL | 0.87 ± 0.09 | 0.78 ± 0.06 | 0.76 ± 0.06 |
| CD 40 Ligand, ng/mL | 0.94 ± 0.19 | 0.49 ± 0.06 | 0.74 ± 0.27 |
| Carcinoembryonic Antigen, ng/mL | 1.55 ± 0.27 | 1.64 ± 0.32 | 1.49 ± 0.36 |
| Creatine Kinase-MB, ng/mL | 0.26 ± 0.07 | 0.42 ± 0.12 | 0.30 ± 0.07 |
| C Reactive Protein, μg/mL | 1.77 ± 0.38 | 1.85 ± 0.29 | 1.77 ± 0.26 |
| Epidermal growth factor, ng/mL | 496.11 ± 148.25 | 220.82 ± 47.70 | 251.67 ± 48.22 |
| Epithelial derived-neutrophil-activating protein, ng/mL | 2.87 ± 0.78 | 1.42 ± 0.33 | 1.68 ± 0.41 |
| EN-RAGE, ng/mL | 15.07 ± 8.48 | 3.71 ± 0.95 | 3.45 ± 0.99 |
| Eotaxin-1, pg/mL | 74.92 ± 12.46 | 69.15 ± 14.60 | 71.37 ± 14.78 |
| Factor VII, ng/mL | 584.25 ± 68.84 | 594.15 ± 67.73 | 548.70 ± 64.71 |
| Ferritin, ng/mL | 158.83 ± 63.78 | 138.39 ± 55.02 | 137.76 ± 59.13 |
| Fibroblast growth factor-basic, pg/mL | 111.70 ± 26.20 | 94.45 ± 18.79 | 102.81 ± 19.33 |
| Fibrinogen, mg/mL | 4.85 ± 0.29 | 4.70 ± 0.32 | 4.81 ± 0.29 |
| Granulocyte colony-stimulating factor, pg/mL | 6.21 ± 0.80 | 5.85 ± 0.76 | 5.63 ± 1.12 |
| Growth hormone, ng/mL | 2.96 ± 1.41 | 2.99 ± 1.07 | 1.71 ± 0.79 |
| Glutathione S-Transferase, ng/mL | 0.55 ± 0.04 | 0.55 ± 0.06 | 0.56 ± 0.02 |
| Haptoglobin, mg/mL | 1.41 ± 0.23 | 1.20 ± 0.26 | 1.26 ± 0.18 |
| ICAM-1, ng/mL | 114.32 ± 14.33 | 111.77 ± 12.54 | 105.01 ± 13.81 |
| Immunoglobulin A, mg/mL | 2.37 ± 0.55 | 2.18 ± 0.57 | 2.14 ± 0.54 |
| Immunoglobulin E, ng/mL | 28.89 ± 7.06 | 39.80 ± 15.23 | 28.89 ± 6.20 |
| Immunoglobulin M, mg/mL | 1.87 ± 0.23 | 1.83 ± 0.25 | 1.85 ± 0.23 |
| Interleukin-10, pg/mL | 11.46 ± 1.67 | 10.97 ± 1.17 | 10.92 ± 2.07 |
| Interleukin-12p 70, pg/mL | 59.32 ± 1.98 | 58.33 ± 1.43 | 59.91 ± 2.15 |
| Interleukin-13, pg/mL | 61.56 ± 6.36 | 60.69 ± 6.13 | 59.52 ± 6.77 |
| Interleukin-15, ng/mL | 0.53 ± 0.08 | 0.46 ± 0.07 | 0.45 ± 0.09 |
| Interleukin-16 pg/mL | 808.10 ± 289.02 | 360.15 ± 32.15 | 404.90 ± 32.28 |

TABLE 8-continued

Effect of limonin glucoside (LG) supplementation on plasma concentrations of biomarkers for human chronic diseases (Rules Based Medicine human multiple analyte panel 1.6).

| Variable | End baseline | End placebo | End LG |
|---|---|---|---|
| Interleukin-18, pg/mL | 277.75 ± 52.02 | 241.90 ± 27.59 | 237.45 ± 24.67 |
| Interleukin-1 beta, pg/mL | 0.45 ± 0.07 | 0.47 ± 0.05 | 0.50 ± 0.14 |
| Interleukin-1 receptor antagonist, pg/mL | 210.29 ± 63.56 | 109.18 ± 18.13 | 105.05 ± 14.03 |
| Interleukin-3, ng/mL | 0.05 ± 0.02 | 0.03 ± 0.01 | 0.05 ± 0.01 |
| Interleukin-4, pg/mL | 78.75 ± 13.53 | 64.58 ± 7.68 | 62.87 ± 8.35 |
| Interleukin-5, pg/mL | 4.39 ± 0.67 | 3.68 ± 0.66 | 3.80 ± 0.77 |
| Interleukin-7, pg/mL | 58.99 ± 8.10 | 49.94 ± 7.61 | 51.27 ± 7.39 |
| Interleukin-8, pg/mL | 18.02 ± 4.20 | 11.07 ± 1.27 | 11.26 ± 1.25 |
| Insulin, μIU/mL | 7.85 ± 5.41 | 2.80 ± 0.54 | 2.94 ± 0.53 |
| Leptin, ng/mL | 14.97 ± 3.94 | 15.18 ± 4.72 | 15.00 ± 4.12 |
| Apolipoprotein a, μg/mL | 105.92 ± 60.73 | 136.73 ± 86.99 | 110.78 ± 57.76 |
| Monocyte chemotactic protein-1, pg/mL | 177.55 ± 15.95 | 165.49 ± 25.02 | 164.84 ± 16.25 |
| Monocyte derived chemokine, pg/mL | 435.15 ± 40.29 | 431.30 ± 43.56 | 426.10 ± 40.45 |
| Macrophage inflammatory protein-1α, pg/mL | 107.81 ± 10.81 | 108.62 ± 12.24 | 106.76 ± 12.39 |
| Macrophage inflammatory protein-1β, pg/mL | 201.24 ± 31.18 | 176.25 ± 32.62 | 183.58 ± 36.53 |
| Matrix metalloproteinase-2, μg/mL | 2.22 ± 0.17 | 2.26 ± 156.07 | 2.20 ± 156.40 |
| Matrix metalloproteinase-2, ng/mL | 171.84 ± 62.97 | 124.00 ± 25.67 | 76.01 ± 22.46 |
| Myeloperoxidase, ng/mL | 317.03 ± 101.50 | 141.78 ± 14.50 | 147.83 ± 22.42 |
| Myoglobin, ng/mL | 17.78 ± 4.20 | 17.51 ± 5.21 | 14.94 ± 2.39 |
| Plasminogen activator inhibitor-1, ng/mL | 87.74 ± 20.32 | 56.85 ± 8.97 | 69.86 ± 15.86 |
| Prostatic Acid Phosphatase, ng/mL | 0.26 ± 0.04 | 0.18 ± 0.02 | 0.17 ± 0.02 |
| Pregnancy associated plasma protein A, mIU/mL | 0.02 ± 0.00 | 0.02 ± 0.00 | 0.02 ± 0.00 |
| Prostate-Specific Antigen, Free, ng/mL | 0.34 ± 0.11 | 0.36 ± 0.12 | 0.31 ± 0.11* |
| T-cell specific protein, RANTES, ng/mL | 26.34 ± 7.80 | 12.75 ± 2.63 | 16.48 ± 3.62 |
| Serum amyloid P-component, μg/mL | 18.19 ± 1.45 | 17.95 ± 1.53 | 16.61 ± 0.94 |
| Stem Cell Factor, pg/mL | 385.85 ± 41.56 | 288.55 ± 25.73 | 351.05 ± 50.76 |
| Serum glutamic oxaloacetic transaminase, μg/mL | 9.43 ± 1.76 | 9.58 ± 1.73 | 9.67 ± 1.64 |
| Sex hormone binding globulin, nmol/L | 30.98 ± 4.36 | 29.71 ± 5.02 | 33.29 ± 5.40 |
| Thyroxine Binding Globulin, μg/mL | 48.56 ± 2.82 | 47.16 ± 2.52 | 46.51 ± 2.84 |
| Tissue factor, ng/mL | 0.49 ± 0.03 | 0.48 ± 0.04 | 0.45 ± 0.03 |
| Tissue inhibitor of metalloproteinases-1, ng/mL | 96.18 ± 15.06 | 79.56 ± 6.17 | 87.97 ± 8.38 |
| Tumor necrosis factor receptor-like 2, ng/mL | 4.10 ± 0.31 | 3.87 ± 0.25 | 3.83 ± 0.25 |
| Tumor necrosis factor α, pg/mL | 4.16 ± 0.62 | 4.92 ± 1.13 | 3.58 ± 0.68 |
| Thrombopoietin, ng/mL | 2.69 ± 0.55 | 1.34 ± 0.20 | 1.40 ± 0.22 |
| Thyroid Stimulating Hormone, μIU/mL | 1.78 ± 0.22 | 1.74 ± 0.17 | 1.72 ± 0.30 |
| Vascular cell adhesion molecule-1, ng/mL | 511.20 ± 49.12 | 510.40 ± 51.48 | 508.80 ± 49.79 |
| Vascular endothelial growth factor, pg/mL | 748.80 ± 111.00 | 661.75 ± 46.29 | 883.55 ± 268.15 |
| Von Willebrand Factor, μg/mL | 30.93 ± 2.39 | 30.22 ± 4.11 | 30.03 ± 3.09 |

Data are Mean ± SEM (n = 10). Comparisons between the ends of placebo and LG treatments were made by SAS mixed models using baseline data as the covariate. None of the response variables were significantly different between the two treatments except, complement C3 (p = 0.014), prostate specific antigen (p = 0.053). Tumor necrosis factor α (p = 0.085), matrix metalloproteinase-9 (p = 0.118) and serum amyloid P (p = 0.188) did not attain significance but showed trends for decrease. For other details see legend for table 2 and methods section.

Conclusions for Example 1

LG supplementation (500 mg/d, 56 days) did not adversely affect parameters of CBC (Table 2) CMP (Table 3) and MAP 1.6 (Table 8). It was well tolerated and it did not have any serious adverse effects.

LG supplementation did not alter the concentrations of a number of blood lipids and lipoproteins tested in our study (Table 4) and the particle sizes and concentrations of large, medium, and small fractions of VLDL, HDL, and LDL (Table 5). Our results regarding the effects of LG on blood lipids differ from those showing an increase in HDL cholesterol (see e.g., Kurowska E M, et al. (2000) The American journal of clinical nutrition. 72:1095-100.) or a decrease in LDL cholesterol with orange juice (see e.g., Cesar T B, et al. (2010) Nutr Res. 30:689-94). The effects of orange juice on HDL- and LDL-cholesterol may have been mediated through components other than LG (such as other limonoids or flavonoids). Since purified citrus flavonoids hesperidin and naringin did not alter serum total- and LDL cholesterol in another study with hypercholesterolemic men and women (see e.g., Demonty I, et al. (2010) The Journal of nutrition. 140:1615-20), the claimed effects of orange juice on LDL- and HDL-cholesterol may have resulted from limonoids other than LG.

A recent study has shown that adding citrus peel extract to the diets of db/db mice ameliorated hyperglycemia and hepatic steatosis (see e.g., Park H J, et al. J Nutr Biochem. 2013 February; 24(2):419-27). Since this extract contained a mixture of limonoids and flavonoids, the active ingredient (s) is not known. In another study with mice fed high fat diets, 0.2% purified nomilin prevented the high fat diet induced obesity and hyperglycemia by activating TGR5, while purified limonin did not activate TGR5 (see e.g., Ono E, et al. (2011). Biochemical and biophysical research communications. 410: 677-81). Results from another study with Hep G2 cell line claimed that limonin significantly decreased Apo B secretion (see e.g., Borradaile N M, et al. (1999) Lipids. 1999; 34:591-8.), but we did not find any change in the plasma concentrations of Apo B (Table 4).

The effects of LG on the plasma concentrations as well as the ex-vivo secretion of a number of pro-inflammatory cytokines by PBMNC were also investigated (Tables 6-8). Circulating concentrations of none of the cytokines were significantly altered by LG treatment. There was a trend for decrease in the ex-vivo secretions of IL-1β, IL-2, IL-4, and IL-6, TNF α, and IFN γ, but none of those changes attained significance.

While LG did not decrease the concentrations of commonly used markers of inflammation in our study, however, unexpectedly it decreased serum concentrations of several novel hepatic markers that have recently been recognized to be associated with inflammation. These markers include GGT, ALA, ALP and C3. LG treatment decreased circulating activities of GGT (33.8%, p=0.001), ALT (13.1%, p=0.041), and ALP (10.1%, p=0.025) when compared with corresponding values at the end of placebo treatment (Table 3). It did not significantly decrease circulating concentration of AST. Without being bound by theory, this may be because ALT is found primarily in liver, while AST is also found in skeletal muscle and erythrocytes (see e.g., Oh R C, et al. (2011) American family physician. 84:1003-8). Generally elevations in ALT are more specific for hepatic injury than elevations in AST. Circulating concentration of C3 was 4.8% and 6.4% lower at the end of LG treatment as compared with the corresponding concentrations at the end of placebo treatment when determined in serum and plasma by two separate analytical methods (p=0.055, Table 6, and (p=0.014, Table 8). Thus, even if the changes in C3 concentrations are modest, those are consistent within serum and plasma and within two separate analytical methods. Besides the percentage changes even the absolute concentrations of C3 determined by two separate methods are very close.

Liver is the major source for the circulating GGT, and ALT, ALP, and C3, although they are also produced by other tissues. GGT is a transmembrane enzyme which is found in secretory tissues like liver, kidney, pancreas, heart, and brain (see e.g., Kazemi-Shirazi L, et al. (2007) Clinical chemistry. 53:940-6). Major source of circulating GGT is liver (see e.g., Corti A, et al. (2010) Anticancer research. 30:1169-81). GGT causes the transfer of gamma glutamyl group from peptides to an acceptor which may be an amino acid, peptide and even water. Originally recognized role of GGT is the metabolism of extracellular glutathione (GSH) (glutamylcysteinylglycine) where it transfers the glutamyl group to an amino acid and forms cystenylglycine and glutamyl amino acid. Cystenylglycine can enter the cell and reutilized for GSH synthesis or hydrolyzed to cysteine and glycine. Because of its role in GSH synthesis, GGT has traditionally been considered as a component of the cell protection system against oxidative stress (see e.g., Pompella A, et al. (2007) Current opinion in pharmacology. August; 7:360-6). However, a number of recent studies have shown that the metabolism of GSH by GGT can exert pro-oxidant effects on mitochondria, cytochromes P450, xanthine oxidase and NADPH oxidase systems (see e.g., Pompella A, et al. (2007) supra). Thiol group of cysteinylglyceine produced by the membrane GGT from GSH acts as a pro-oxidant extracellularly particularly in the presence of $Fe^{3+}$ and $Cu^{2+}$. This increases production of reactive oxygen species (ROS) and inflammation (see e.g., Corti A, et al. (2010) supra). Increased production of ROS can also cause random damage to macromolecules and initiate cancer and other diseases. A fine equilibrium exits between antioxidant and pro-oxidant functions of GGT, and the latter may prevail in GGT-overexpressing cells and in the presence of metal ions (see e.g., Pompella A, et al. (2004) Clinical chemistry and laboratory medicine: CCLM/FESCC. 2004; 42:1085-91). Cysteinylglyceine also induces leukotriene induced inflammation (see e.g., Mistry D, et al. (2010) Copd. 2010; 7:285-90).

ALT is found primarily in hepatic parenchymal cells and is leaked into the blood with injury to the liver. It is also found in other tissues including skeletal muscle and erythrocytes but at much lower concentrations than liver. Most common abnormality in liver function tests is a combined increase in ALT and GGT. It has been proposed that elevated ALT and GGT are markers of inflammation and oxidative stress, independent of their relationship with metabolic syndrome (see e.g., Yamada J, et al. (2006) Atherosclerosis. 2006; 189:198-205; Bo S, et al. (2005) World journal of gastroenterology. 11:7109-17, Mistry D, et al. (2010) supra). ALP is present practically in all tissues, particularly high in intestinal epithelium, kidney tubules, bone, liver, and placenta. Enzyme activity in plasma comes primarily from liver or biliary duct. Both ALP and GGT are elevated in biliary disease; GGT is not elevated in bone disease, while ALP is elevated. Thus, increase in both ALP and GGT can verify that increase in ALP is due to liver and not bone. Besides liver, C3 is also produced by activated macrophages and adipose tissue (see e.g., Kojima C, et al. (2012) Journal of atherosclerosis and thrombosis. 19:854-61). It is involved in the activation of complement system which plays pivotal role in inflammation and in bridging innate and adaptive immunity (see e.g., Walport M J. (2001) The New England journal of medicine. 344:1140-4.). LG treatment may have decreased the production of C3, GGT, ALT and ALP by tissues other than liver, however, concomitant decrease in 4 enzymes produced by the liver suggests that LG decreased the production of these enzymes by the liver. Alternately, it may have increased their clearance from the plasma.

In addition to reduction in the activity of GGT, decrease in circulating free PSA also suggests that LG reduces the incidence of prostate cancer. LG supplementation decreased the circulating free PSA approximately 14% when the data were pooled for men and women (p=0.053, n=10) or analyzed separately for men (p=0.059, n=5) (Table 8). Serum concentration of free PSA in women was only 5-10% of the concentration in men. These data show that a decrease in PSA was observed in all 5 men. Since circulating levels of PSA also increase with benign prostate hypertrophy (BPH), it is possible that the decrease in PSA seen in our study may have resulted from decreased prostate size.

Thus, we have discovered for the first time that supplementing the diets of overweight and obese human subjects with purified LG significantly decreased circulating concentrations of liver enzymes (GGT, ALT, ALP, and C3). Indeed, a small dose of LG (0.5 g/d) reduced the circulating concentration of GGT by 33%, indicating that purified limonin glucoside is very effective in reducing GGT activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of treating a subject suffering from NAFLD, the method comprising orally administering to the subject a therapeutically effective amount of purified limonin glucoside (LG) or a pharmaceutically acceptable salt thereof.

2. The method of claim 1, wherein the administering results in a reduction in fat content of liver.

3. The method of claim 1, wherein the administering results in a reduction in the incidence of or progression of cirrhosis.

4. The method of claim 1, wherein the administering results in a reduction in the incidence of hepatocellular carcinoma.

5. A method of treating a subject suffering from a chronic disease, wherein the chronic disease is a member selected from the group consisting of Alcoholic Liver Disease (ALD), Non-Alcoholic Fatty Liver Disease (NAFLD), and chronic kidney disease (CKD) or a combination thereof, the method comprising administering to the subject a therapeutically effective amount of purified limonin gluco side (LG) or a pharmaceutically acceptable salt thereof.

6. The method of claim 5, wherein the daily dose of (LG) or a pharmaceutically acceptable salt thereof is about 0.25-19.0 g/day.

7. The method of claim 5, wherein the dose is 0.5 gram per day.

8. The method of claim 5, wherein the purified limonin glucoside or a pharmaceutically acceptable salt thereof, is administered at a frequency of 4 or less times per day.

9. The method of claim 7, wherein the purified limonin glucoside or a pharmaceutically acceptable salt thereof, is administered two times per day.

10. The method of claim 5, wherein the purified limonin glucoside or a pharmaceutically acceptable salt thereof, is administered orally.

\* \* \* \* \*